(12) United States Patent
Danho et al.

(10) Patent No.: US 9,409,961 B2
(45) Date of Patent: Aug. 9, 2016

(54) CELL PENETRATING PEPTIDES TO TARGET EIF4E

(71) Applicant: Hoffmann-La Roche Inc., Nutley, NJ (US)

(72) Inventors: Waleed Danho, Del Mar, CA (US); Nader Fotouhi, Basking Ridge, NJ (US); Yi Han, Morristown, NJ (US); Wajiha Khan, Boonton, NJ (US); Francesca Milletti, New York, NY (US); Huifeng Niu, Scotch Plains, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 37 days.

(21) Appl. No.: 14/411,951

(22) PCT Filed: Jul. 5, 2013

(86) PCT No.: PCT/EP2013/064209
§ 371 (c)(1),
(2) Date: Dec. 30, 2014

(87) PCT Pub. No.: WO2014/009259
PCT Pub. Date: Jan. 16, 2014

(65) Prior Publication Data
US 2015/0166621 A1 Jun. 18, 2015

Related U.S. Application Data

(60) Provisional application No. 61/669,207, filed on Jul. 9, 2012.

(51) Int. Cl.
*C07K 14/47* (2006.01)
(52) U.S. Cl.
CPC ......... *C07K 14/4702* (2013.01); *C07K 2319/10* (2013.01)

(58) Field of Classification Search
None
See application file for complete search history.

(56) References Cited

U.S. PATENT DOCUMENTS

2012/0172315 A1 7/2012 Cosson et al.

FOREIGN PATENT DOCUMENTS

| WO | 0078803 | 12/2000 |
|---|---|---|
| WO | 2006078942 | 7/2006 |
| WO | 2010080248 | 7/2010 |
| WO | 2011136744 | 11/2011 |

OTHER PUBLICATIONS

The International Search Report and Written Opinion, mailed on Nov. 14, 2013, in the corresponding PCT Appl. No. PCT/EP2013/064209.
Brown et al., "Stabilizing the eIF4G1 α-Helix Increases Its Binding Affinity with eIF4E: Implications for Peptidomimetic Design Strategies," J. Mol. Biol. (2011) 405, 736-753.
Jia et al., "Cap-Dependent Translation Initiation Factor eIF4E: An Emerging Anticancer Drug Target," Medicinal Research Reviews, 32, No. 4, 786-814, 2012.
Holz et al., "mTOR and S6K1 Mediate Assembly of the Translation Preinitiation Complex through Dynamic Protein Interchange and Ordered Phosphorylation Events," Cell, vol. 123, 569-580, Nov. 18, 2005.

*Primary Examiner* — Amber D Steele
*Assistant Examiner* — Schuyler Milton

(57) ABSTRACT

The present invention provides compounds to disrupt the eIF4E-eIF4G interaction and pharmaceutically acceptable salts of such compounds. Generally, the compounds are cell-penetrating peptides which bind mammalian initiation factor eIF4E (CPP-eIF4E), wherein the peptide comprises an amino acid sequence selected from the group consisting of SEQ ID NOS: 7, 9-11, 12-26, 27-44 and 45-51. More preferably, the amino acid sequence comprises at least 9 to about 40 amino acids and the mammalian initiation factor eIF4E is human initiation factor eIF4E.

14 Claims, 2 Drawing Sheets

CELL PENETRATING PEPTIDES TO TARGET EIF4E

CROSS-REFERENCE TO RELATED APPLICATIONS

This application is a National Stage Application of PCT/EP2013/064209 filed Jul. 5, 2013, which claims priority from U.S. Provisional Patent Application No. 61/669,207, filed on Jul. 9, 2012. The priority of both said PCT and U.S. Provisional Patent Application are claimed. Each of the prior mentioned applications is hereby incorporated by reference herein in its entirety.

FIELD OF THE INVENTION

The present invention comprises cell penetrating peptides that inhibit the protein-protein interaction between the eukaryotic translation initiation factors eIF4E and eIF4G. eIF4E is an promising therapeutic target that makes fundamental contributions to tumorigenesis by regulating the expression of key cancer-related genes at the post-transcriptional levels. The peptides of the invention, or pharmaceutically acceptable salts thereof, may be used for reducing tumor growth and tumor size.

BACKGROUND OF THE INVENTION

Eukaryotic initiation factor 4E (eIF4E) is a 24 kDa protein that plays a key role in the initiation of translation of mRNA. At the initiation of mRNA translation, eIF4E binds to the 7-methylguanosine cap at the 5' end of mRNAs, and forms a complex (called eIF4F) with the scaffolding protein eIF4G and the helicase eIF4A. The formation of this complex is required for the initiation of cap-dependent translation of mRNAs and therefore the binding of eIF4E to eIF4G is a critical event in this process.

eIF4E has been identified as a promising target in the field of oncology because of a number of pieces of evidentiary data that implicate its essential role in transformation and tumorigenesis. For example, overexpression of eIF4E in transgenic mice promotes tumor formation (see Silvera, D. et al. *Nat. Rev. Cancer* 2010, 10, 254-266 and references cited therein; see also Konicek, B. W. et al. *Cell Cycle* 2008, 7, 2466-2471 and references cited therein). Overexpression of eIF4E has been observed in a variety of human cancers including breast, lung, skin, colon, prostate, and cervical cancers, and is associated with poor prognosis and decreased survival (see for example, Zhou, S. et al. *BMC Cancer* 2006, 6, 231). Expression of eIF4E is associated with disease progression in endometrial cancer, and siRNA knockdown of eIF4E inhibits cell growth in endometrial cancer cells (Choi, H. C. et al. *J. Cancer Res. Clin. Oncol.* 2011, 137, 463-469). A helically stabilized peptide based on the sequence of eIF4G binds to eIF4E, and also shows inhibition of cap-dependent translation in a reporter gene assay in MCF-7 cells, although at a high concentration (Brown, C. J. et al. *J. Mol. Biol.* 2011, 405, 736-753). A set of peptides that bind to eIF4E and cause apoptosis in chronic lymphocytic leukemia cell lines has been disclosed in a patent application (Cosson, B. et al. WO 2010100351).

Small molecule inhibitors of the eIF4E-eIF4G interaction have been disclosed by Gerhard Wagner and colleagues (Moerke, N. J. et al. *Cell* 2007, 128, 257-267). The activity of these compounds has been demonstrated in vivo in a rat model of fear consolidation, which depends on the formation of the eIF4F complex (Hoeffer, C. A. et al. *Proc. Nat. Acad. Sci. USA* 2011, 108, 3383-3388). A number of small molecule inhibitors of the eIF4E-eIF4G interaction have been disclosed also by Min and colleagues as part of the NIH Molecular Libraries Program (HTS for inhibitors of Eukaryotic Translation Initiation, Probe Report by J. Min, Grant Number 1 R03 MH081216-01, Probe PubChem Compound Identifier: 16195554, Jun. 23 2009).

A series of eIF4E antagonists that bind to the cap binding site of eIF4E has been disclosed by Carston Wagner and colleagues (Jia, Y. et al. *Eur. J. Med. Chem.* 2010, 45, 1304-1313 and Jia, Y. PhD dissertation, University of Minnesota, January 2011; AN 2011:418548). Additional compounds that bind to the $m^7$-GTP site were disclosed at the 240th National Meeting of the American Chemical Society (Aug. 22-26, 2010) (see Kopecky, D. et al. MEDI-227; abstracted in Chemical Abstracts as AN 2010:1011833). Further compounds that bind to the $m^7$-GTP site were disclosed in patent application (Brown, C. J. WO 2010138084).

Because eIF4E is a cytosolic target, a peptide- or small molecule-eIF4E antagonist requires that the compound be delivered in the cytosol, for example by crossing the cell membrane by passive diffusion or through some active mechanism such as endocytosis. However since most peptides are not cell-penetrating, this is a challenge for peptide-based antagonists.

Cell-penetrating peptides (CPPs) are a class of peptides with the ability to convey various, otherwise impermeable, macromolecules across the plasma membrane of cells in a relatively non-toxic fashion. The CPP peptides are typically between 5 and about 30 amino acids (aa) in length with a cationic, amphipathic, or hydrophobic nature. Notable examples of cell-penetrating peptides include Tat, Penetratin, and Transportan. (Fawell, S. et al. *Proc. Natl. Acad. Sci.* 1994, pp 664-668; Theodore, L. et al. *J. Neurosci.* 1995, pp 7158-7167; Pooga, M. et al. *FASEB J.* 1998, pp 67-77). A cell penetrating peptide such as Tat can be attached to an effector peptide, or the effector peptide can be intrinsically cell-penetrating. Examples of effector peptides intrinsically cell-penetrating include Arf(1-22) and p28, among others (Johansson, H. J. et al. *Mol. Ther.* 2007, 16(1), pp 115-123; Taylor, B. N. et al. *Cancer Res.* 2009, 69 (2), pp. 537-546)

The present invention generally relates to peptides that are cell-penetrating and with the ability to bind to eIF4E and disrupt the eIF4E-eIF4G interaction, and to enter a tumor cell line.

SUMMARY OF THE INVENTION

The present invention provides compounds to disrupt the eIF4E-eIF4G interaction and pharmaceutically acceptable salts of such compounds. In a general embodiment, the compounds are cell-penetrating peptides which bind mammalian initiation factor eIF4E (CPP-eIF4E), wherein the peptide comprises an amino acid sequence selected from the group consisting of SEQ ID NOS: 7, 9-11, 12-26, 27-44 and 45-51. More preferably, the amino acid sequence comprises at least 9 to about 40 amino acids and the mammalian initiation factor eIF4E is human initiation factor eIF4E.

In a preferred embodiment, the compounds are cell-penetrating peptides which bind mammalian initiation factor eIF4E (CPP-eIF4E), wherein the peptide comprises an amino acid sequence of SEQ ID NOS: 7, 9 and 10-44, wherein said amino acid sequence further comprises, in part, an amino acid sequence motif selected from the group consisting of:
YxxxxZZxF (SEQ ID NO: 1), wherein Y is tyrosine (Tyr), x is any amino acid, Z is leucine (Leu) or norleucine (Nle), and F is phenylalanine (Phe), or
Tyr-Trp-Leu-Leu-Ala-Leu-Phe-Val-Tyr (SEQ ID NO. 2). More preferably, the amino acid sequence is at least 9 to about 40 amino acids and the mammalian initiation factor eIF4E is human initiation factor eIF4E.

In an alternative preferred embodiment, the present invention provides an isolated and purified polypeptide of about 9 to about 40 amino acids, consisting of a first peptide and an optional second peptide, wherein the first peptide
i. comprises an amino acid sequence of at least 9 amino acids,
ii. has the ability to bind mammalian initiation factor eIF4E, and more preferably human initiation factor eIF4E,
iii. and wherein the first peptide further comprises, in part, an amino acid sequence motif of Ac-R1-Tyr-R2-R3-R4-R5-Leu-Leu-R6-Phe-R7-NH2 (SEQ ID NO: 3), wherein
R1 is selected from the group consisting of Lys-Lys, Lys-Gln, Lys-Arg and Lys-Ala
R2 is Asp, Asn or Ala
R3 is Arg
R4 is Glu, Lys, Cys, Ala, Gln or Phe
R5 is Phe
R6 is Asp, Cys, Ala or Aib
R7 is Gln-Phe-R8-R9-R10-R11 (SEQ ID NO:4), wherein R8 is Met, Ala, (D)Met, Nle, R9 is Pro, (D)Pro, Ala or none, R10 is Ala, (D)Ala or none and R11 is the optional second peptide comprising a cell penetrating peptide (CPP) of about 5 to about 20 amino acids.

In yet another preferred embodiment, the present invention provides an isolated and purified peptide of at least 9 to about 40 amino acids, consisting of a first and an optional second polypeptide, wherein the first peptide
comprises an amino acid sequence of at least 9 amino acids,
ii. has the ability to bind mammalian initiation factor eIF4E (more preferably human initiation factor eIF4E),
iii. and wherein the first peptide comprises, in part, an amino acid motif of Tyr-Trp-Leu-Leu-Ala-Leu-Phe-Val-Tyr (Seq ID NO. 2)
and the optional second peptide is a cell penetrating peptide (CPP).

In yet another preferred embodiment, the present invention provides SEQ ID NOS. 45-51, which are cell-penetrating peptides which bind mammalian initiation factor eIF4E (CPP-eIF4E), more preferably human initiation factor eIF4E. Alternatively, the present invention also provides SEQ ID NOS. 52-85 which have the ability to bind mammalian initiation factor eIF4E, more preferably human initiation factor eIF4E.

In yet a still another preferred embodiment, the present invention provides an isolated and purified peptide of at least 9 to about 40 amino acids, consisting of a first and an optional second polypeptide, wherein the first peptide
i. comprises an amino acid sequence of at least 9 amino acids,
ii. has the ability to bind mammalian initiation factor eIF4E, more preferably human initiation factor eIF4E,
and wherein the first peptide comprises, comprises an amino acid sequence selected from the group consisting of SEQ ID NOS:52-85
and the optional second peptide is a cell penetrating peptide (CPP).

DETAILED DESCRIPTION OF THE INVENTION

Figure 1:
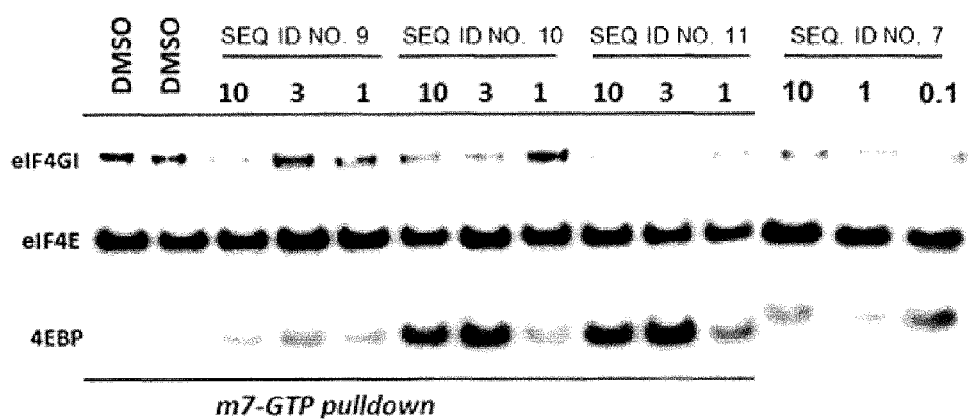
FIG. 1 shows the result of the in vitro cellular proof of mechanisms for peptides with SEQ ID 7, 9, 10, and 11 based on the m7-GTP pulldown assay.
Figure 2:
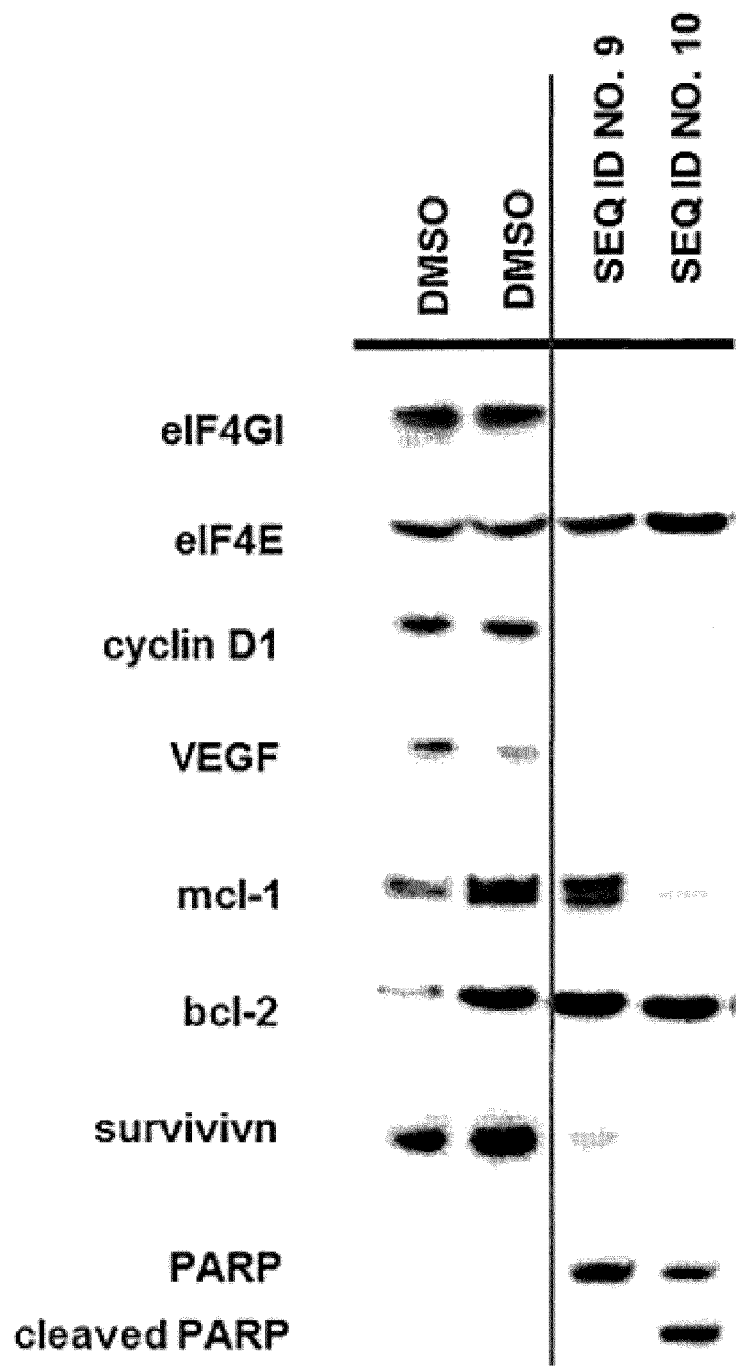
FIG. 2 shows that peptides with SEQ ID 9 and 10 inhibit downstream target gene expression and induce apoptosis.

The present invention discloses compounds which are cell-penetrating peptides which bind mammalian initiation factor eIF4E (CPP-eIF4E), wherein the peptide comprises an amino acid sequence selected from the group consisting of SEQ ID NOS: 7, 9-11, 12-26, 27-44 and 45-52. More preferably, the amino acid sequence comprises at least 9 to about 40 amino acids and the mammalian initiation factor eIF4E is human initiation factor eIF4E.

More particularly, the present invention discloses compounds which can bind eIF4E, and more particularly wherein said compounds are cell-penetrating peptides which can bind mammalian initiation factor eIF4E (CPP-eIF4E), wherein the peptide comprises an amino acid sequence selected from the group consisting of SEQ ID NOS: 7, 9 and 10-44, wherein said amino acid sequence further comprises, in part, an amino acid sequence motif selected from the group consisting of:
a) YxxxxzzxF (SEQ ID NO: 1), wherein Y is tyrosine (Tyr), x is any amino acid, z is leucine (Leu) or norleucine (Nle), and F is phenylalanine (Phe), or
b) Tyr-Trp-Leu-Leu-Ala-Leu-Phe-Val-Tyr (SEQ ID NO. 2). More preferably, the amino acid sequence is at least 9 to about 40 amino acids and the mammalian initiation factor eIF4E is human initiation factor eIF4E.

In a further embodiment, the cell-penetrating peptides which can bind mammalian initiation factor eIF4E (CPP-eIF4E) comprise, or alternatively consist of, an amino acid sequence of SEQ ID NOS: 7, 12 and 13-26 of the amino acid motif of Ac-R1-Tyr-R2-R3-R4-R5-Leu-Leu-R6-Phe-R7-NH2 (SEQ ID NO:3), wherein R2-R6 is any amino acid and R1 and R7 is any amino acid or amino acid sequence, wherein further R1 or R7 is an amino acid sequence of about 8 to about 25 amino acids comprising a cell penetrating peptide (this embodiment is disclosed as SEQ ID NO: 89). In a more particularly preferred embodiment,
R1 is selected from the group consisting of Lys-Lys, Lys-Gln, Lys-Arg and Lys-Ala
R2 is Asp, Asn or Ala
R3 is Arg
R4 is Glu, Lys, Cys, Ala, Gln or Phe
R5 is Phe
R6 is Asp, Cys, Ala or Aib
R7 is Gln-Phe-R8-R9-R10-R11 (SEQ ID NO:4), wherein R8 is Met, Ala, (D)Met, Nle, R9 is Pro, (D)Pro, Ala or none, R10 is Ala, (D)Ala or none and R11 is a cell penetrating peptide (CPP) of about 5 to about 20 amino acids. In a more preferred embodiment, R11 is Val-Tyr-Asp-Leu-Gly-Leu-Arg-Arg-Leu-Arg-Gln-Arg-Arg-Arg-Leu-Arg-Arg (SEQ ID NO:5).

In a further embodiment, the cell penetrating peptide which can bind eIF4E comprises the peptide of formula I Ac-Lys-Arg-Tyr-Asp-Arg-Glu-Phe-Leu-Leu-Ala-Phe-Gln-Phe-Nle-R11 (SEQ ID NO:6), wherein R11 is a cell penetrating peptide (CPP) of about 5 to about 20 amino acids. In a more preferred embodiment, R11 is Val-Tyr-Asp-Leu-Gly-Leu-Arg-Arg-Leu-Arg-Gln-Arg-Arg-Arg-Leu-Arg-Arg (SEQ ID NO:5).

More particularly and preferably, the peptide of the present invention consists of SEQ ID NO:7. (Ac-Lys-Arg-Tyr-Asp-Arg-Glu-Phe-Leu-Leu-Ala-Phe-Gln-Phe-Nle-Val-Tyr-Asp-Leu-Gly-Leu-Arg-Arg-Leu-Arg-Gln-Arg-Arg-Arg-Leu-Arg-Arg-NH$_2$).

Other more preferred peptides of the present invention which comprise SEQ ID NOS 1 and/or 3 above, and additionally are cell-penetrating, comprise the following sequences: SEQ ID NOS 7, 12, 13-26 as shown in Table 2. SEQ ID NOS 52-85, which comprise or consist of SEQ ID NOS 1 and/or 3 above, but are not cell-penetrating, are listed in Table 1.

In an alternative embodiment, the cell-penetrating peptides which can bind mammalian initiation factor eIF4E (CPP-eIF4E) comprise, or alternatively consist of, an amino acid sequence of SEQ ID NOS: 9-11 and 27-44, wherein further said sequence comprises the amino acid motif of Tyr-Trp- Leu-Leu-Ala-Leu-Phe-Val-Tyr (SEQ ID NO. 2). More particularly, the amino acid sequence comprises the amino acid motif of Ac-Met-Ala-R1-Leu-R2-Tyr-Trp-Leu-Leu-Ala-Leu-Phe-Val-Tyr-Met-Trp-Thr-Asp-Leu-R3-Leu-R4-Lys-Lys-Arg-Pro-Lys-Pro-NH2 (SEQ ID NO. 8), wherein R1 is Lys or Asn, R2 is Lys or Ala, R3 is Leu or Arg and R4 is Phe or t-ButAla. More preferably, the amino acid sequence is selected from the group consisting of SEQ ID NOs 9, 10 or 11. ((II) Ac-Met-Ala-Lys-Leu-Lys-Tyr-Trp-Leu-Leu-Ala-Leu-Phe-Val-Tyr-Met-Trp-Thr-Asp-Leu-Leu-Leu-Phe-Lys-Lys-Arg-Pro-Lys-Pro-NH2 (SEQ ID NO: 9); (III): Ac-Met-Ala-Asn-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 (SEQ ID NO: 10); (IV) Ac-Met-Ala-Asn-Leu-Ala-Tyr-Trp-Leu-Leu-Ala-Leu-Phe-Val-Tyr-Met-Trp-Thr-Asp-Leu-Arg-Leu-tBuAla-Lys-Lys-Arg-Pro-Lys-Pro-NH2 (SEQ ID NO: 11)).

More particularly, the peptides of the present invention which comprise SEQ ID NO.2 above comprise the following sequences: SEQ ID NOS 9-11 and 27-44 as shown in Table 2a (Table 2a lists examples of peptides of the present invention that are CPP, bind to eif4e and have the motif of SEQ ID NO.2).

In yet a further embodiment, the peptides of the present invention which bind eif4e and are cell-penetrating comprise SEQ ID NOS: 45-51 as reflected in Table 3.

Alternatively, the present invention discloses an isolated and purified polypeptide of about 9 to about 40 amino acids, comprising, or alternatively consisting of, a first peptide and an optional second peptide, wherein the first peptide i. comprises an amino acid sequence of at least 9 amino acids, ii. has the ability to bind mammalian initiation factor eIF4E (more preferably human initiation factor eIF4E), iii. and wherein the first peptide further comprises, in part, an amino acid sequence motif of YxxxxLLxF (SEQ ID NO: 90), wherein Y is tyrosine (Tyr) or phenylalanine (Phe), x is any amino acid, L is leucine (Leu), and F is phenylalanine (Phe), and wherein the optional second peptide is a cell penetrating peptide (CPP).

In an alternative and more preferred embodiment, the present invention discloses an isolated and purified polypeptide of about 9 to about 40 amino acids, comprising, or alternatively consisting of, a first peptide and an optional second peptide, wherein the first peptide i. comprises an amino acid sequence of at least 9 amino acids, ii. has the ability to bind mammalian initiation factor eIF4E (more preferably human initiation factor eIF4E), iii. and wherein the first peptide further comprises, in part, an amino acid sequence of 9 to about 30 amino acids of the amino acid motif of Ac-R1-Tyr-R2-R3-R4-R5-Leu-Leu-R6-Phe-R7-NH2, (SEQ ID NO:3) wherein R2-R6 is any amino acid and R1 and R7 is any amino acid or amino acid sequence, wherein further R1 or R7 comprises the optional CPP (this embodiment is disclosed as SEQ ID NO: 89). In a more preferred embodiment, R1 is selected from the group consisting of Lys-Lys, Lys-Gln, Lys-Arg and Lys-Ala; R2 is Asp, Asn or Ala; R3 is Arg; R4 is Glu, Lys, Cys, Ala, Gln or Phe; R5 is Phe; R6 is Asp, Cys, Ala or Aib; R7 is Gln-Phe-R8-R9-R10-R11 (SEQ ID NO: 4), wherein R8 is Met, Ala, (D)Met, Nle, R9 is Pro, (D)Pro, Ala or none, R10 is Ala, (D)Ala or none and R11 is an optional cell penetrating peptide (CPP) of about 5 to about 20 amino acids. In a yet more preferred embodiment, the polypeptide comprises or consists of Ac-Lys-Arg-Tyr-Asp-Arg-Glu-Phe-Leu-Leu-Ala-Phe-Gln-Phe-Nle-R11 (Seq ID NO 6). More particularly, the first peptide of the embodiment which comprise or consist of SEQ ID NO1 above comprise the following sequences: SEQ ID NOS 52-85 as shown in Table 1 (Peptides which bind eIF4E but which are not cell-penetrating).

Alternatively, the invention also provides an isolated and purified peptide of at least 9 to about 40 amino acids, consisting of a first and an optional second polypeptide, wherein the first peptide i. comprises an amino acid sequence of at least 9 amino acids, ii. has the ability to bind mammalian initiation factor eIF4E (more preferably human initiation factor eIF4E), iii. and wherein the first peptide comprises, in part, an amino acid motif of Tyr-Trp-Leu-Leu-Ala-Leu-Phe-Val-Tyr (Seq ID NO. 2) and the optional second peptide is a cell penetrating peptide (CPP).

In another embodiment, the invention also provides an isolated and purified peptide of at least 9 to about 40 amino acids, consisting of a first and an optional second polypeptide, wherein the first peptide comprises
  i) an amino acid sequence of at least 9 amino acids, and
  ii) has the ability to bind mammalian initiation factor eIF4E (more preferably human initiation factor eIF4E), and further
  iii) comprises an amino acid sequence of SEQ ID NOS:53-86
and the optional second peptide is a cell penetrating peptide (CPP). Representative examples of such first peptides are listed in Table 3.

DEFINITIONS

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

A cell-penetrating peptide (CPP) of the invention generally denotes a peptide of about 5 to about 30 amino acids that is able to penetrate cell membranes and to translocate different cargoes into cells. More preferably, CPP as herein defined additionally excludes so-called "stapled" peptides, defined as wherein the sequences comprise two or more unnatural or man-made amino acids and additionally are connected via a side-chain bridge or cyclic peptide.

The phrase "peptide(s) which bind eIF4e" or "peptide(s) which is/are capable of binding eIF4E" denotes those groups of peptides which are positive (defined herein as where IC50<20 uM) in a biochemical assay where the target is eIF4e.

The term "eIF4E" or eukaryotic initiation factor 4E denotes a 24 kDa protein, more preferably human eIF4E comprising amino acid sequence (SEQ ID NO 86). More specifically, human eIF4E consists of amino acid sequence 28-217 (aa 28-217) VAN PEHYIKHPLQ NRWALWFFKN DKSKTWQANLRLISKFDTVE DFWALYNHIQ LSSN-LMPGCD YSLFKDGIEP MWEDEKNKRG GRWL-ITLNKQ QRRSDLDRFW LETLLCLIGE SFDDYSDDVC GAVVNVRAKG DKIAIWTTEC ENREAVTHIG RVYK-ERLGLP PKIVIGYQSH ADTATKSGST TKNRFVV (SEQ ID NO: 87). Alternatively, human eIF4E (residues 28-217 above) can be expressed in *E. coli* with an additional 6 histidines encoded after the C-terminal residue of eIF4E to aid in purification (SEQ ID NO: 88).

The term "Amino acid motif" denotes a conserved sequence of amino acids (e.g. Y-LL-F). This sequence may also include gaps to indicate the number of residues that separate each amino acid of the motif.

The term "Amino acid" denotes an organic compound of general formula $NH_2CHRCOOH$ where R can be any organic group. Specifically, the term amino acid may refer to natural and unnatural (man-made) amino acids, such as Aib=alpha-aminoisobutyric acid; tBuAla=Tert-butyl Alanine; Thr-OBzl=Threonine benzyl ester; 5Ava=5-aminovaleric acid; Asp=D=Aspartic Acid; Ala=A=Alanine; Arg=R=Arginine; Asn=N=Asparagine; Gly=G=Glycine; Glu=E=Glutamic Acid; Gln=Q=Glutamine; His=H=Histidine; Ile=I=Isoleucine; Leu=L=Leucine; Lys=K=Lysine; M=Methionine; Mamb=(3-aminomethyl) benzoic acid; Mamp=Met=(3-aminomethyl) phenyl acetic acid; Nle=Norleucine; Nva=Norvaline; Phe=F=Phenylalanine; Pro=P=Proline; Ser=S=Serine; Thr=T=Threonine; Trp=W=Tryptophan; Tyr=Y=Tyrosine; and Val=V=Valine.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "IC50 value" or the term "half maximal inhibitory concentration" (IC50) denotes the concentration of a particular compound required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099).

All peptide sequences mentioned herein are written according to the usual convention whereby the N-terminal amino acid is on the left and the C-terminal amino acid is on the right, unless noted otherwise. A short line between two amino acid residues indicates a peptide bond. Where the amino acid has isomeric forms, it is the L form of the amino acid that is represented unless otherwise expressly indicated.

For convenience in describing this invention, the conventional and nonconventional abbreviations for the various amino acids residues are used. These abbreviations are familiar to those skilled in the art, but for clarity are listed below: Aib=alpha-aminoisobutyric acid; tBuAla=Tert-butyl Alanine; Thr-OBzl=Threonine benzyl ester; 5Ava=5-aminovaleric acid; Asp=D=Aspartic Acid; Ala=A=Alanine; Arg=R=Arginine; Asn=N=Asparagine; Gly=G=Glycine; Glu=E=Glutamic Acid; Gln=Q=Glutamine; His=H=Histidine; Ile=I=Isoleucine; Leu=L=Leucine; Lys=K=Lysine; Met=M=Methionine; Mamb=(3-aminomethyl) benzoic acid; Mamp=Met=(3-aminomethyl) phenyl acetic acid; Nle=Norleucine; Nva=Norvaline; Phe=F=Phenylalanine; Pro=P=Proline; Ser=S=Serine; Thr=T=Threonine; Trp=W=Tryptophan; Tyr=Y=Tyrosine; and Val=V=Valine.

Also for convenience, and readily known to one skilled in the art, the following abbreviations or symbols are used to represent the moieties, reagents and the like used in this invention:
$Et_2O$ diethyl ether
hr(s) hour(s)
TIS triisopropylsilane
(D)Tyr D-tyrosine
(D)Phe D-phenylalanine
SSA succinimidyl succinamide
Fmoc 9-fluorenylmethyloxycarbonyl
DMF dimethylformamide
DIPEA N,N-diisopropylethylamine
TFA trifluoroacetic acid
HOBT N-hydroxybenzotriazole
BOP benzotriazol-1-yloxy-tris-(dimethylamino)phosphonium-hexafluorophosphate
HBTU 2-(1H-benzotriazole-1-yl)-1,1,3,3-tetramethyluronium-hexafluorophosphate
NMP N-methyl-pyrrolidone
FAB-MS fast atom bombardment mass spectrometry
ES-MS electro spray mass spectrometry The compounds of the present invention may be readily synthesized by any known conventional procedure for the formation of a peptide linkage between amino acids. Such conventional procedures include, for example, any solution phase procedure permitting a condensation between the free alpha amino group of an amino acid or fragment thereof having its carboxyl group and other reactive groups protected and the free primary carboxyl group of another amino acid or fragment thereof having its amino group or other reactive groups protected.

Such conventional procedures for synthesizing the novel compounds of the present invention include, for example, any solid phase peptide synthesis method. In such a method the synthesis of the novel compounds can be carried out by sequentially incorporating the desired amino acid residues one at a time into the growing peptide chain according to the general principles of solid phase methods. Such methods are disclosed in, for example, Merrifield, R. B., J. Amer. Chem. Soc. 85, 2149-2154 (1963); Barany et al., The Peptides, Analysis, Synthesis and Biology, Vol. 2, Gross, E. and Meienhofer, J., Eds. Academic Press 1-284 (1980), which are incorporated herein by reference.

During the synthesis of peptides, it may be desired that certain reactive groups on the amino acid, for example, the alpha-amino group, a hydroxyl group, and/or reactive side chain groups, be protected to prevent a chemical reaction therewith. This may be accomplished, for example, by reacting the reactive group with a protecting group which may later be removed. For example, the alpha amino group of an amino acid or fragment thereof may be protected to prevent a chemical reaction therewith while the carboxyl group of that amino acid or fragment thereof reacts with another amino acid or fragment thereof to form a peptide bond. This may be followed by the selective removal of the alpha amino protecting group to allow a subsequent reaction to take place at that site, for example with the carboxyl group of another amino acid or fragment thereof.

Alpha amino groups may, for example, be protected by a suitable protecting group selected from aromatic urethane-type protecting groups, such as allyloxycarbony, benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropyloxycarbonyl, 9-fluorenylmethyloxycarbonyl (Fmoc) and p-methoxybenzyloxycarbonyl (Moz); and aliphatic urethane-type protecting groups, such as t-butyloxycarbonyl (Boc), diisopropylmethyloxycarbonyl, isopropyloxycarbonyl, and allyloxycarbonyl. In an embodiment, Fmoc is used for alpha amino protection.

Hydroxyl groups (OH) of the amino acids may, for example, be protected by a suitable protecting group selected from benzyl (Bzl), 2,6-dichlorobenztl (2,6 diCl-Bzl), and tert-butyl (t-Bu). In an embodiment wherein a hydroxyl group of tyrosine, serine, or threonine is intended to be protected, t-Bu may, for example, be used.

Epsilon-amino acid groups may, for example, be protected by a suitable protecting group selected from 2-chloro-benzyloxycarbonyl (2-Cl-Z), 2-bromo-benzyloxycarbonyl (2-Br-Z), allycarbonyl and t-butyloxycarbonyl (Boc). In an embodiment wherein an epsilon-amino group of lysine is intended to be protected, Boc may, for example, be used.

Beta- and gamma-amide groups may, for example, be protected by a suitable protecting group selected from 4-methyltrityl (Mtt), 2,4,6-trimethoxybenzyl (Tmob), 4,4'-dimethoxyditiyl (Dod), bis-(4-methoxyphenyl)-methyl and Trityl (Trt). In an embodiment wherein an amide group of asparagine or glutamine is intended to be protected, Trt may, for example, be used.

Indole groups may, for example, be protected by a suitable protecting group selected from formyl (For), Mesityl-2-sulfonyl (Mts) and t-butyloxycarbonyl (Boc). In an embodiment wherein the indole group of tryptophan is intended to be protected, Boc may, for example, be used.

Imidazole groups may, for example, be protected by a suitable protecting group selected from Benzyl (Bzl), t-butyloxycarbonyl (Boc), and Trityl (Trt). In an embodiment wherein the imidazole group of histidine is intended to be protected, Trt may, for example, be used.

Solid phase synthesis may be commenced from the C-terminal end of the peptide by coupling a protected alpha-amino acid to a suitable resin. Such a starting material can be prepared by attaching an alpha-amino-protected amino acid by an ester linkage to a p-benzyloxybenzyl alcohol (Wang) resin, or by an amide bond between an Fmoc-Linker, such as p-((R, S)-α-(1-(9H-fluoren-9-yl)-methoxyformamido)-2,4-dimethyloxybenzyl)-phenoxyacetic acid (Rink linker), and a benzhydrylamine (BHA) resin. Preparation of the hydroxymethyl resin is well known in the art. Fmoc-Linker-BHA resin supports are commercially available and generally used when the desired peptide being synthesized has an unsubstituted amide at the C-terminus.

In an embodiment, peptide synthesis is microwave assisted. Microwave assisted peptide synthesis is an attractive method for accelerating the solid phase peptide synthesis. This may be performed using Microwave Peptide Synthesizer, for example a Liberty peptide synthesizer (CEM Corporation, Matthews, N.C.). Microwave assisted peptide synthesis allows for methods to be created that control a reaction at a set temperature for a set amount of time. The synthesizer automatically regulates the amount of power delivered to the reaction to keep the temperature at the set point.

Typically, the amino acids or mimetic are coupled onto the Fmoc-Linker-BHA resin using the Fmoc protected form of amino acid or mimetic, with 2-5 equivalents of amino acid and a suitable coupling reagent. After coupling, the resin may be washed and dried under vacuum. Loading of the amino acid onto the resin may be determined by amino acid analysis of an aliquot of Fmoc-amino acid resin or by determination of Fmoc groups by UV analysis. Any unreacted amino groups may be capped by reacting the resin with acetic anhydride and diisopropylethylamine in methylene chloride.

The resins are carried through several repetitive cycles to add amino acids sequentially. The alpha amino Fmoc protecting groups are removed under basic conditions. Piperidine, piperazine or morpholine (20-40% v/v) in DMF may be used for this purpose. In an embodiment, 20% piperidine in DMF is utilized.

Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino)phosphonium hexafluorophosphate (BOP), bromo-tris-pyrrolidino-phosphonium hexafluorophosphate (PyBroP) 2-(1H-benzotriazole-1-yl)-1,1,3,3-tetramethyluronium hexafluorophosphate (HBTU), and diisopropylcarbodiimide (DIC). In an embodiment, the reagent is HBTU or DIC. Other activating agents are described by Barany and Merrifield (in The Peptides, Vol. 2, J. Meienhofer, ed., Academic Press, 1979, pp 1-284). Various reagents such as 1 hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. In an embodiment, HOBT is added. Following synthesis of the peptide, the blocking groups may be removed and the peptide cleaved from the resin. For example, the peptide-resins may be treated with 100 μL ethanedithiol, 100 μl dimethylsulfide, 300 μL anisole, and 9.5 mL trifluoroacetic acid, per gram of resin, at room temperature for 180 min. Alternatively, the peptide-resins may be treated with 1.0 mL triisopropyl silane and 9.5 mL trifluoroacetic acid, per gram of resin, at room temperature for 90 min. The resin may then be filtered off and the peptide precipitated by addition of chilled ethyl ether. The precipitates may then be centrifuged and the ether layer decanted.

Purification of the crude peptide may be, for example, performed on a Shimadzu LC-8A system by high performance liquid chromatography (HPLC) on a reverse phase $C_{18}$ Column (50×250 mm, 300 Å, 10 μm). The peptides may be dissolved in a minimum amount of water and acetonitrile and injected on to a column. Gradient elution may be generally started at 2%-90% B over 70 minutes, (buffer A: 0.1% TFA/$H_2O$, buffer B: 0.1% TFA/$CH_3CN$) at a flow rate of 60 ml/min. UV detection set at 220/280 nm. The fractions containing the products may be separated and their purity judged on Shimadzu LC-10AT analytical system using reverse phase Pursuit $C_{18}$ column (4.6×50 mm) at a flow rate of 2.5 ml/min., gradient (2-90%) over 10 min. [buffer A: 0.1% TFA/H$_2$O, buffer B: 0.1% TFA/CH$_3$CN)]. Fractions judged to be of high purity may then be pooled and lyophilized.

Yet another possible method for making the peptides of the present invention would be the following protocol for peptide synthesis at room temperature. In this procedure, generally the following steps would be taken:

| Step | Reagent | Time |
| --- | --- | --- |
| 1 | DMF | 2 × 30 sec |
| 2 | 20% piperidine/DMF | 5 min |
| 3 | 20% piperidine/DMF | 15 min |
| 4 | DMF | 2 × 30 sec |
| 5 | iPrOH | 2 × 30 sec |
| 6 | DMF | 3 × 30 sec |
| 7 | coupling | 60 min-18 hours |
| 8 | DMF | 2 × 30 sec |
| 9 | iPrOH | 1 × 30 sec |
| 10 | DMF | 1 × 30 sec |
| 11 | CH$_2$Cl$_2$ | 2 × 30 sec |

Solvents for all washings and couplings are measured to volumes of 10-20 ml/g resins. Coupling reactions throughout the synthesis can be monitored by the Kaiser Ninhydrin test to determine extent of completion (Kaiser et at. Anal. Biochem. 34, 595-598 (1970)). Any incomplete coupling reactions are either recoupled with freshly prepared activated amino acid or capped by treating the peptide resin with acetic anhydride as described above. The fully assembled peptide-resins are dried in vacuum for several hours, generally overnight, depending on the amount of solvent left.

The amino acid sequences of this invention may also be synthesized by methods known to those of ordinary skill in the art. Such methods include, but are not limited to, microwave peptide synthesis (Murray J. K., Aral J., and Miranda L. P. Solid-Phase Peptide Synthesis Using Microwave Irradiation In Drug Design and Discovery. Methods in Molecular Biology, 2011, Volume 716, 73-88, DOI: 10.1007/978-1-61779-012-6_5) and solid state synthesis of amino acid sequences (Steward and Young, Solid Phase Peptide Synthesis, Freemantle, San Francisco, Calif. (1968)). An exemplary solid state synthesis method is the Merrifield process (Merrifield, Recent Progress in Hormone Res., 23:451 (1967)).

The compounds of the present invention, as herein described, can also be provided in the form of pharmaceutically acceptable salts. Examples of preferred salts are those formed with pharmaceutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids (e.g., hydrochloric acid), sulfuric acid, or phosphoric acid and the like. Any procedure for obtaining a pharmaceutically acceptable salt known to a skilled artisan can be used.

All publications, patent applications, patents, and other references mentioned herein are incorporated by reference in their entirety.

EXAMPLES

The invention will be more fully understood by reference to the following examples. They should not, however, be construed as limiting the scope of the invention.

All solvents, isopropanol (iPrOH), methylene chloride (CH$_2$Cl$_2$), dimethylformamide (DMF) and N-methylpyrrolidone (NMP) were purchased from Fisher or Burdick & Jackson and were used without additional distillation.

Trifluoroacetic acid was purchased from Halocarbon or Fluka and used without further purification.

Diisopropylcarbodiimide (DIC) and diisopropylethylamine (DIPEA) were purchased from Fluka or Aldrich and used without further purification.

Hydroxybenzotriazole (HOBT), dimethylsulfide (DMS) and 1,2-ethanedithiol (EDT) were purchased from Sigma Chemical Co. and used without further purification.

Protected amino acids were generally of the L configuration and were obtained commercially from Bachem or Neosystem.

Purity of these reagents was confirmed by thin layer chromatography, NMR and melting point prior to use.

Benzhydrylamine resin (BHA) was a copolymer of styrene—1% divinylbenzene (100-200 or 200-400 mesh) obtained from Bachem or Advanced Chemtech. Total nitrogen content of these resins were generally between 0.3-1.2 meq/g.

High performance liquid chromatography (HPLC) was conducted on an automated Shimadzu HPLC with CLASS-VP-7.3 software system. Analytical HPLC was performed in reversed phase mode using Pursuit $C_{18}$ columns (4.5×50 mm).

Preparative HPLC separations were run on reversed phase Varian (Pursuit) or Waters (Xtera or Xbridge) $C_{18}$ columns (50×250 mm).

Example 1

The following example describes a representative exemplary protocol for microwave peptide synthesis.

A Liberty peptide synthesizer (CEM Corporation, Matthews, N.C.) was programmed for double coupling and capping by modification of the preloaded 0.25 mmol cycle using the software supplied by the manufacturer. The microwave editor was used to program microwave power methods for use during the Fmoc deprotection, amino acid coupling and capping with acetic anhydride. The default cycles for amino acid addition and final deprotection were selected in the cycle editor and were automatically loaded while creating the peptide.

The synthesis was carried out on a 0.25 mmol scale using Fmoc-Linker-BHA resin (450 mg, 0.25 mmol; available from AnaSpec, Inc., Fremont, Calif.). Deprotection was performed with a 20% piperidine in DMF solution. All coupling reactions were performed with 0.5M HBTU and 2M N-methyl morpholine (NMM) and were capped with 25% acetic anhydride in DMF after each amino acid coupling (protocol 2). Each deprotection, coupling and capping reaction was done using microwave at 75° C. for 360 seconds at 35 watts power and Nitrogen bubbling.

For each amino acid coupling, the following 0.25 mmol coupling cycle was used.
Protocol 2
Transfer resin to vessel
Add 20% Piperidine Deprotection (10 mL)
Microwave method for 1$^{st}$ deprotection 30 sec at 75° C. max
Wash resin with DMF (10 mL)
Microwave method for 2$^{nd}$ deprotection 180 sec at 75° C. max
Wash resin 3× with DMF (10 mL)
Add 0.2M Amino acid (5 mL)
Add 0.5M Activator (HBTU) (2 mL)
Add 2M Activator base (NMM) (1 mL)
Microwave method for Coupling 6 minutes at 75° C. max.
Wash resin with DMF (10 mL)

Add 0.2M Amino acid (5 mL)
Add 0.5M Activator (HBTU) (2 mL)
Add 2M Activator base (NMM) (1 mL)
Microwave method for Coupling 6 minutes at 75° C. max.
Wash resin 3× with DMF (10 mL)

The peptide was capped after the last amino acid coupling with 25% acetic anhydride in DMF (protocol 3)
Protocol 3
Wash resin 3× with DMF (10 mL)
Add 20% Piperidine Deprotection (10 mL)
Microwave method for $1^{st}$ deprotection 30 sec at 75° C. max
Wash resin with DMF (10 mL)
Microwave method for $2^{nd}$ deprotection 180 sec at 75° C. max
Wash resin 3× with DMF (10 mL)
Add capping (Acetic Anhydride 10 mL)
Microwave Method (capping) 180 sec at 75° C. max
Wash resin 3× with DMF (10 mL)

Example 2

Synthesis of Ac-Met-Ala-Lys-Leu-Lys-Tyr-Trp-Leu-Leu-Ala-Leu-Phe-Val-Tyr-Met-Trp-Thr-Asp-Leu-Leu-Leu-Phe-Lys-Lys-Arg-Pro-Lys-Pro-NH$_2$ (SEQ ID NO: 9)

The above peptide was synthesized using Fmoc chemistry on CEM microwave peptide synthesizer. The synthesizer was programmed for double coupling using the modules described in protocols 2 and 3 of Example 1. The synthesis was carried out on a 0.25 mmol scale using the Fmoc Rink Amide MBHA resin (Sub: 0.45 meq/g; used 450 mg). At the end of the synthesis, the resin was transferred to a reaction vessel on a shaker for cleavage. The peptide was cleaved using 17 mL of 97% TFA (3% water) and 1 mL of TIS and propane thiol (1:2) at room temperature for 1.5 hrs. The deprotection solution was added to 100 mL cold Et$_2$O, and washed with 1 mL TFA and 30 mL cold Et$_2$O to precipitate the peptide. The peptide was centrifuged in 2×50 mL polypropylene tubes. The precipitates from the individual tubes were combined in a single tube and washed 3 times with cold Et$_2$O and dried in a desiccator under house vacuum.

The crude peptide was purified by preparative HPLC (Shimadzu) on a Xtera C18-Column (250×50 mm, 10 µm particle size) and eluted with a linear gradient of 10-99% B (buffer A: 0.1% TFA/H2O; buffer B: 0.1% TFA/CH$_3$CN) in 90 min., flow rate 60 mL/min, and detection 220/280 nm. The fractions were collected and were checked by analytical HPLC. All analytical runs were performed on Shimadzu HPLC using C18 reverse phase Waters Xtera/pursuit 4.6×50 mm columns using gradient from 10-99% using A: 0.1% Water/TFA and B:0.1% Acetonitrile/TFA. Fractions containing pure product were combined and lyophilized to yield 197 mg (19%) of a white amorphous powder. (ES)+-LCMS m/e calculated ("calcd") for $C_{177}H_{273}N_{39}O_{34}S_2$ 3555.52. found 35552.49.

Example 3

Synthesis of Ac-Met-Ala-Asn-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH$_2$ (SEQ ID NO: 10)

Fmoc Rink Amide MBHA resin (450 mg, 0.25 mmol) was subjected to solid phase synthesis and purification by generally following the procedure in example 2 to yield 73 mg (7%) of white amorphous powder. (ES)+-LCMS m/e calculated ("calcd") for $C_{173}H_{261}N_{41}O_{35}S_2$ 3527.39. found 3527.31.

Example 4

Synthesis of Ac-Met-Ala-Asn-Leu-Ala-Tyr-Trp-Leu-Leu-Ala-Leu-Phe-Val-Tyr-Met-Trp-Thr-Asp-Leu-Arg-Leu-tBuAla-Lys-Lys-Arg-Pro-Lys-Pro-NH$_2$ (SEQ ID NO: 11)

Fmoc Rink Amide MBHA resin (450 mg, 0.25 mmol) was subjected to solid phase synthesis and purification by generally following the procedure in example 2 to yield 54 mg (5%) of white amorphous powder. (ES)+-LCMS m/e calculated ("calcd") for $C_{170}H_{265}N_{41}O_{35}S_2$ 3507.39. found 3506.98.

Example 5

Synthesis of certain sequences (SEQ ID NOS: 7, 12-21 and 23-30, 45-46, 52-67 and 81-83) were synthesized [by CSBio (Menlo Park, Calif., USA)] via solid state synthesis. (Steward and Young, Solid Phase Peptide Synthesis, Freemantle, San Francisco, Calif. (1968). The following general exemplary method for the solid state synthesis for said sequences is described
Material:

All chemicals and solvents such as DMF (Dimethylformamide), DCM (Methylene Chloride), DIEA (Diisopropylethylamine), and piperidine were purchased from VWR and Aldrich, and used as purchased without further purification. Mass spectra were recorded with Electrospray ionization mode. The automated stepwise assembly of protected amino acids was constructed on a CS 336X series peptide synthesizer (C S Bio Company, Menlo Park, Calif., USA) with Rink Amide MBHA resin as the polymer support. N-(9-fluorenyl)methoxycarbonyl (Fmoc) chemistry was employed for the synthesis. The protecting groups for Fmoc amino acids (AAs) were as follows, Arg: (Pbf), Asn/Gln/Cys/His: (Trt), Asp/Glu: (OtBu), Lys/Trp: (Boc), Ser/Thr/Tyr: (tBu).
Synthesis:

In general, the synthesis route started from deFmoc of pre-loaded Rink Amide resin and coupling/de-protecting of desired AAs according to the given sequences for all the orders. Coupling reagent was DIC/HOBt, and reaction solvents were DMF and DCM. The ratio of peptidyl resin/AA/DIC/HOBT was 1/4/4/4 (mol/mol). After coupling program, DeFmoc was executed using 20% piperidine in DMF. For example, a 0.4 mmol synthesis was performed till the last AA was attached. After deFmoc, the resin was acetylated with Ac2O/DIEA to give N-term Ac sequence.

Fmoc-Rink Amide Resin (0.85 g, 0.4 mmol, sub: 0.47 mm/g, Lot#110810, C S Bio) was mixed in a 25 mL reaction vessel (RV) with DMF (10 mL), and swollen for 10-30 min. The RV was mounted on a CS336 peptide automated synthesizer and the amino acids were loaded onto amino acid (AA) wheel according to the given peptide sequence. HOBt (0.5M in DMF) and DIC (0.5M in DMF) were all pre-dissolved separately in transferrable bottles under N$_2$. Fmoc-amino acids (AAs, 4 eq) were weighed and prelocated as powder on the AA wheel. For example, 0.4 mmol synthesis needed 1.6 mmol of AA. The preset program started from AA dissolving in the AA tube and the solution was pumped thru M-VA to T-VA. HOBt solution was later mixed with AA. N$_2$ bubbling was used to assist mixing. While DIC solution was combined with the AA/HOBt solution, the whole mixture was transferred into the RV with drained resin in 5 min and the coupling started at the same time. After shaking for 3-6 hr, reaction mixture was filtered off and the resin was washed with DMF three times, followed by deFmoc according to the preset program using 20% Pip in DMF. The next AA was attached following the same route. Seven washing steps were done with DMF/DCM alternatively after deFmoc. The coupling process was repeated with the respective building blocks according to the given sequence till the last AA was coupled. Coupling Time: 3-6 hrs for each AA attachment.

After deFmoc of last AA, the resin was acetylated by Ac20/DIEA in DMF.

Cleavage:

The final peptidyl resin (1-1.5 g) was mixed with TFA cocktail (TFA/EDT/TIS/H2O) and the mixture was shaken at room temperature for 4 hr. The cleaved peptide was filtered and the resin was washed by TFA. After ether precipitation and washing, the crude peptide (200-500 mg) was obtained in a yield of 50-90%. The crude peptide was directly purified without lyophilization.

Purification:

Crude peptides, 200-500 mg of acetylated peptides, were dissolved in Buffer A 0.1% TFA in water and ACN, and the peptide solution was loaded onto a C18 column (2 inch) with a prep HPLC purification system. With a flow rate of 25-40 mL/min, the purification was finished in a TFA (0.1%) buffer system with a 60 min gradient. Fractions (peptide purity >95%) containing the expected MW were collected. The prep HPLC column was then washed for at least three void column volumes by 80% Buffer B and equilibrated to 5% Buffer B before next loading.

Lyophilization:

The fractions (purity >90%) were combined and transferred to 1 L lyophilization jars which were deeply frozen by liquid nitrogen. After freezing, the jars were placed onto Lyophilizer (Virtis Freezemobile 35EL) and dried overnight. The vacuum was below 500 mT and chamber temperature was below −60° C. The lyophilisation was completed in 12-18 hrs at room temperature (environment temperature).

Results:

The procedure started with about 0.4 mm synthesis for each sequence. The synthesis yield was around 50-90% and the crude purities ranged from 30-70%. Purification was done in TFA system and final yield was about 10% for each order.

Example 5a

Synthesis of Ac-Lys-Arg-Tyr-Asp-Arg-Glu-Phe-Leu-Leu-Ala-Phe-Gln-Phe-Nle-Val-Tyr-Asp-Leu-Gly-Leu-Arg-Arg-Leu-Arg-Gln-Arg-Arg-Arg-Leu-Arg-Arg-NH$_2$ (SEQ ID NO: 7)

The above peptide was synthesized as per Example 5 above via solid state synthesis. In the specific preparation of SEQ ID NO:7, Fmoc Rink Amide MBHA resin (0.55 g, 0.25 mmol) was subjected to solid phase synthesis and purification by following the procedure in example 5 to yield 17 mg (2.6%). (ES)+-LCMS m/e calculated ("calcd") for $C_{186}H_{307}N_{65}O_{41}$. found 4110.40.

Example 6

A biochemical assay was run to test peptide binding to human eIF4E.

Human eIF4E (aa 28-217, SEQ ID NO: 87) with a C-terminal His tag (HH-eIF4E, SEQ ID NO: 88) was expressed in *E. coli* in inclusion bodies. The protein was solubilized with 8 M urea and purified under denaturing conditions using nickel-charged HisTrap HP columns (GE Healthcare). The protein was refolded by diluting to approximately 0.25 mg/mL with 6 M urea, 20 mM Hepes pH 7.0, 500 mM NaCl, 1 mM DTT, 1 mM EDTA, and 0.5 M arginine.HCl, and then dialyzing overnight into the same buffer without the urea. The protein was further dialyzed into 20 mM Hepes pH 6.5, 50 mM NaCl, 1 mM EDTA, and 1 mM DTT, filtered, and then concentrated using Hitrap SP sepharose FF columns (GE Healthcare). The protein was dialyzed into 20 mM Hepes pH 7.0, 500 mM NaCl, 5 mM DTT, and 10% glycerol and stored at −80° C. until use.

Test peptides (1.6 mM stock in DMSO) were diluted 3 fold in series in DMSO and solutions were diluted 4 fold in Assay Buffer (50 mM NaPi, pH 6.5, 50 mM KCl, 1 mM DTT, 0.004% NP40 and 0.5 mg/ml gammaglobulin). Six microliters per well of diluted peptide solutions and 12 microliters per well of 187.5 nM HH-eIF4E in Assay Buffer were added to 384-well polypropylene microplates (Matrix, Thermal Scientific). Twelve microliters per well of 187.5 nM biotin labeled 4G2 peptide (Ac-Lys-Gln-Tyr-Asp-Arg-Glu-Phe-Leu-Leu-Asp-Phe-Gln-Phe-Met-Pro-Lys(Aha-Bio)-NH2 (SEQ ID NO: 91) 1:2 TFA) in Assay Buffer was added. The samples were incubated at room temperature for 20 minutes.

Six microliters per well of 4.8 nM Eu-streptavidin (Columbia Biosciences) and 48 nM Allophycocyanin-anti His antibody (Columbia Biosciences) in Assay Buffer (without DTT) were then added and the samples were incubated at room temperature for 30 min. Assay signals were monitored by reading emission fluorescence at 665 nm on an Envision Reader (PerkinElmer Life and Analytical Sciences). IC50 values were calculated using Condoseo software (Genedata AG, Basel, Switzerland). For purposes of this invention, IC50 values below 20 µM are considered good, with IC 50 values below 10 µm being preferred and IC 50 values below 5 µM, especially below 1 µM, being most preferred.

Binding affinities—expressed as IC50—were 0.21 µM (SEQ ID NO: 7), 4.404 µM (SEQ ID NO: 9), 6.614 (SEQ ID NO: 10), and 2.373 µM (SEQ ID NO: 11).

Example 7

The following study was conducted to assess the displacement of eIF4G from eIF4E in NCI-H460Cells.

NCI-H460 cells were obtained from ATCC (Manassas, Va.) and were maintained in RPMI-1640 medium containing 10% fetal bovine serum at 37° C. in 5% $CO_2$. Cells were seeded to 6-well plates at a concentration of $0.75 \times 10^6$ cells per well. After 24 hours, DMSO (control) (Sigma-Aldrich D2650) or peptides were added to cells at indicated concentrations and incubated at 37° C. for 3 hours. Treated cells were rinsed with 2 ml ice cold PBS. The plate was placed on ice and 500 µl RIPA lysis buffer (Sigma Aldrich R0278) containing protease inhibitors (Roche Applied Science 04 693 159 001) was added to each well. After 5 minutes the cell monolayer was scraped to remove cells and the lysate was transferred to a 1.5 ml conical tube and incubated on ice for 30 minutes. Each sample was then sonicated for 10 s on ice and insoluble fragments were removed by centrifugation. For the affinity purification of eIF4E and associated proteins, 25 µl of pre-rinsed 7-Methyl-GTP Sepharose™ 4B (GE Healthcare 275025) was added to the clarified lysate and incubated for 16 hours at 4° C. on a rocking platform. The sepharose beads were pelleted at 1000 g and washed twice with RIPA buffer and twice with PBS. Sepharose beads were suspended in 2×LDS sample buffer (InVitrogen NP007) and heated at 95° C. for 5 minutes to elute eIF4E and associated proteins.

Proteins were resolved by electrophoresis on a Bis-Tris 4-12% gradient gel. The gel was soaked for 20 minutes in 2× transfer buffer (InVitrogen NP0006-1) containing 10% methanol before semi-dry electrophoresis transfer of proteins to PVDF membrane. Proteins were detected using antibodies against eIF4G (Cell Signaling Technology #2858), eIF4E (Cell Signaling Technology #9742), and 4E-BP1 (Cell Signaling Technology #9644) at dilutions of 1:1,000, 1:10,000 and 1:5000 respectively. Chemiluminescent signal was generated with enhanced chemiluminescence plus (ECL) (GE Healthcare RPN2132) and detected with Fujifilm LAS-3000 imager.

Example 8

The following lactate dihydrogenase release (LDH) assay was performed to assess peptide cytotoxicity, using CytoTox-ONE™ Homogeneous Membrane Integrity (Catalog number G7890; Promega corporation, Madison Wis.).

Reagent preparation: substrate mix and assay buffer were equilibrated to 22° C. CytoTox-ONE™ Reagent was prepared by adding 11 ml of assay buffer to each vial of substrate mix and gently mixed to dissolve the substrate.

The three following controls were used in the experiment: 1) no-cell control: well without cells to serve as the negative control to determine background fluorescence that might be present; 2) untreated cells Control: well with vehicle (DMSO) treated cells to serve as a control; 3) maximum LDH Release Control: well to determine maximum LDH release was prepared by adding 40 µl of lysis solution to the positive control well.

Cytotoxicity Assay Protocol:
1. NCI-H460 cells were obtained from ATCC (Manassas, Va.) and were maintained in RPMI-1640 medium containing 10% fetal bovine serum at 37° C. in 5% CO2. Cells were seeded to 6-well plates at a concentration of 0.75×106 cells per well 24 hours before the assay.
2. After 24 hours, DMSO (control) or peptides were added to cells at indicated concentrations and incubated at 37° C. for 3 hours. Maximum LDH release control was prepared by the addition of lysis solution at the beginning of treatment period. The value obtained for this control represents 100% LDH release.
3. Assay plates were removed from 37° C. incubator and equilibrated to 22° C. (approximately 20-30 minutes).
4. 100 µl of medium was removed from the control and treated cells and transferred to 96-well plate in triplicate.
5. 100 µl of CytoTox-ONE™ reagent was added to each well and mixed for 30 seconds.
6. The assay plate was incubated at 22° C. for 10 minutes.
7. 50 µl of stop solution was added to each well.
8. The plate was mixed for 10 seconds and fluorescence was recorded with an excitation wavelength of 560 nm and an emission wavelength of 590 nm.

Calculation of Results.

The average fluorescence values of the culture medium background was subtracted from all fluorescence values of experimental wells.

The percent cytotoxicity was calculated using the average fluorescence values from experimental, maximum LDH release, and culture medium background Percent cytotoxicity=100×(Experimental–Culture Medium Background)/(Maximum LDH Release–Culture Medium Background).

With LDH release comparable to the control (<10%), peptides with SEQ ID NOS: 7 and 9-11 are not cytotoxic at concentrations up to 20 µM.

Example 9

The following study was conducted to assess the stability of the compound of Examples 2-4 (SEQ ID NOS: 9, 10 and 11) in Hannover Wistar rat and human plasma after 4 and 24 hours. Approximately, 2.0 mg of the compound of Examples 2-4 (SEQ ID NOS 9, 10 and 11) was weighed out and placed in a 4 mL amber vial. To this was added 1.0 mL DMSO. The vial was carefully vortexed to produce a solution of approximately 600 µM.

Hannover Wistar rat plasma and human plasma (anti-coagulant sodium EDTA) were pre-warmed to 37° C. for 30 minutes in a water bath. The pH of both plasmas was adjusted to pH7.4. 1.5 mL microcentrifuge vials were used.

The stock solution of the compound of Examples 2-4 was diluted into rat or human plasma to a final concentration of 10 µM. The two vials were gently vortexed ensuring proper mixing.

Six new vials were labeled as follows: rat $T_0$, rat $T_4$, rat $T_{24}$, human $T_0$, human $T_4$, human $T_{24}$. To each of these vials, 50 µL of treated plasma was added. The $T_4$ and $T_{24}$ vials were capped and placed in a 37° C. incubator for 4 and 24 hours, respectively.

To each of the two $T_0$ vials, 50 µL of Sorensen buffer and 200 µL 1.0% acetic acid in acetonitrile were added. The $T_0$ vials were then capped, vortexed and centrifuged at 10000×g for 10 minutes. Upon completion of centrifugation, 100 µL of the supernatant of each vial was added to a separate well in a 96-well injection block. 2004 of 0.1% acetic acid in Milli-Q® water (Millipore) was then added to each well.

The above procedure as written with respect to the $T_0$ vials was repeated for the two $T_4$ vials at the 4 hour time point and the $T_{24}$ vials at the 24 hour time point. With each time point a fresh $T_0$ sample was prepared, as described above, to ensure there was no sample degradation.

All samples were analyzed by LC/MS/MS. The resulting chromatographs were processed to obtain peaks areas for each sample. The percent of compound remaining at each time point as compared with the amount present in the comparison $T_0$ sample was calculated.

| | Conc. (10 uM) | | | |
| --- | --- | --- | --- | --- |
| | Rat | | Human | |
| | % Remaining 4 hr | % Remaining 24 hr | % Remaining 4 hr | % Remaining 24 hr |
| SEQ ID 9 | 91.7 | 18.2 | 94.9 | 76.2 |
| SEQ ID 10 | 102 | 23.7 | 99.1 | 45.2 |
| SEQ ID 11 | 89.4 | 24.2 | 103 | 77.0 |

The data indicate that the compounds were stable in rat plasma at 4 hours but slightly below the acceptance range at the 24 hour time point. The peptides were stable for both the 4 hour and the 24 hour time points in human plasma.

Examples 10-83

Synthesis of SEQ ID NOS: 12-85

The following sequences (SEQ ID NOS: 12-85) were prepared according to the general methods of Examples 2 and 5 (CSBIO) as indicated. Mass spectrometry and yield results, as available, are indicated for each SEQ ID NO.

10. Synthesis of Ac-Met-Val-Lys-Tyr-Lys-Ile-Gly-Ser-Leu-Leu-Leu-Phe-Leu-Phe-Val-Ala-Met-Trp-Ser-Asp-Val-Gly-Leu-Cys-Lys-Lys-Arg-Pro-Lys-Pro-NH2 (SEQ ID NO: 12)

Fmoc Rink Amide MBHA resin (0.61 g, 0.25 mmol) was subjected to solid phase synthesis and purification by following the procedure in example 5 to yield 53 mg (6%). (ES)+-LCMS m/e calculated ("calcd") for $C_{167}H_{270}N_{40}O_{36}S_3$. found 3510.41.

11. Synthesis of Ac-Met-Val-Lys-Ser-Lys-Tyr-Gly-Ser-Trp-Ile-Leu-Leu-Leu-Phe-Val-Ala-Met-Trp-Ser-Asp-Val-Gly-Leu-Cys-Lys-Lys-Arg-Pro-Lys-Pro-NH2 (SEQ ID NO: 13)

Fmoc Rink Amide MBHA resin (0.61 g, 0.25 mmol) was subjected to solid phase synthesis and purification by following the procedure in example 5 to yield 128 mg (14.5%). (ES)+-LCMS m/e calculated ("calcd") for $C_{166}H_{265}N_{41}O_{37}S_3$. found 3523.37.

12. Synthesis of Ac-Met-Tyr-Lys-Ser-Lys-Ile-Leu-Leu-Trp-Phe-Leu-Val-Leu-Phe-Val-Ala-Met-Trp-Ser-Asp-Val-Gly-Leu-Cys-Lys-Lys-Arg-Pro-Lys-Pro-NH2 (SEQ ID NO: 14)

Fmoc Rink Amide MBHA resin (0.61 g, 0.25 mmol) was subjected to solid phase synthesis and purification by following the procedure in example 5 to yield 85 mg (9.3%). (ES)+-LCMS m/e calculated ("calcd") for $C_{176}H_{277}N_{41}O_{36}S_3$. found 3639.57.

13. Synthesis of Ac-Met-Val-Lys-Ser-Lys-Ile-Tyr-Ser-Trp-Ile-Leu-Leu-Leu-Phe-Phe-Ala-Met-Trp-Ser-Asp-Val-Gly-Leu-Cys-Lys-Lys-Arg-Pro-Lys-Pro-NH2 (SEQ ID NO: 15)

Fmoc Rink Amide MBHA resin (0.61 g, 0.25 mmol) was subjected to solid phase synthesis and purification by following the procedure in example 5 to yield 87 mg (9.6%). (ES)+-LCMS m/e calculated ("calcd") for $C_{174}H_{273}N_{41}O_{37}S_3$. found 3627.52.

14. Synthesis of Ac-Met-Ala-Asn-Leu-Gly-Tyr-Trp-Leu-Leu-Ala-Leu-Phe-Val-Tyr-Met-Trp-Thr-Asp-Leu-Leu-Leu-Phe-Lys-Lys-Arg-Pro-Lys-Pro-NH2 (SEQ ID NO: 16)

Fmoc Rink Amide MBHA resin (0.61 g, 0.25 mmol) was subjected to solid phase synthesis and purification by following the procedure in example 5 to yield 100 mg (11.5%). (ES)+-LCMS m/e calculated ("calcd") for $C_{171}H_{258}N_{38}O_{35}S_2$. found 3470.28.

15. Synthesis of Ac-Met-Val-Lys-Tyr-Lys-Ile-Ala-Ser-Leu-Leu-Leu-Phe-Leu-Phe-Val-Ala-Met-Trp-Ser-Asp-Val-Ala-Leu-Ala-Lys-Lys-Arg-Pro-Lys-Pro-NH2 (SEQ ID NO: 17)

Fmoc Rink Amide MBHA resin was subjected to solid phase synthesis and purification by following the procedure in example 5. (ES)+-LCMS m/e calculated ("calcd") for $C_{169}H_{274}N_{40}O_{36}S_2$. found 3506.4.

16. Synthesis of Ac-Met-Val-Lys-Tyr-Lys-Ile-Ala-Ser-Leu-Leu-Leu-Phe-Leu-Phe-Val-Ala-Met-Trp-Ser-Asp-Val-Lys-Leu-Lys-Lys-Lys-Arg-Pro-Lys-Pro-NH2 (SEQ ID NO: 18)

Fmoc Rink Amide MBHA resin was subjected to solid phase synthesis and purification by following the procedure in example 5. (ES)+-LCMS m/e calculated ("calcd") for $C_{175}H_{288}N_{42}O_{36}S_2$. found 3620.59.

17. Synthesis of Ac-Met-Tyr-Lys-Ser-Lys-Ile-Leu-Leu-Trp-Phe-Leu-Val-Leu-Phe-Val-Ala-Met-Trp-Ser-Asp-Val-Ala-Leu-Ala-Lys-Lys-Arg-Pro-Lys-Pro-NH2 (SEQ ID NO: 19)

Fmoc Rink Amide MBHA resin was subjected to solid phase synthesis and purification by following the procedure in example 5. (ES)+-LCMS m/e calculated ("calcd") for $C_{177}H_{279}N_{41}O_{36}S_2$. found 3621.53.

18. Synthesis of Ac-Met-Val-Lys-Ser-Lys-Ile-Tyr-Ser-Trp-Ile-Leu-Leu-Leu-Phe-Phe-Ala-Met-Trp-Ser-Asp-Val-Ala-Leu-Ala-Lys-Lys-Arg-Pro-Lys-Pro-NH2 (SEQ ID NO: 20)

Fmoc Rink Amide MBHA resin was subjected to solid phase synthesis and purification by following the procedure in example 5. (ES)+-LCMS m/e calculated ("calcd") for $C_{175}H_{275}N_{41}O_{37}S_2$. found 3609.48.

19. Synthesis of Ac-Met-Val-Lys-Ser-Lys-Ile-Tyr-Ser-Trp-Ile-Leu-Leu-Leu-Phe-Phe-Ala-Met-Trp-Ser-Asp-Val-Lys-Leu-Lys-Lys-Lys-Arg-Pro-Lys-Pro-NH2 (SEQ ID NO: 21)

Fmoc Rink Amide MBHA resin was subjected to solid phase synthesis and purification by following the procedure in example 5. (ES)+-LCMS m/e calculated ("calcd") for $C_{181}H_{289}N_{43}O_{37}S_2$. found 3723.67.

20. Synthesis of Ac-Lys-Arg-Tyr-Asp-Arg-Glu-Phe-Leu-Leu-Ala-Phe-Gln-Phe-Nle-Arg-Arg-Leu-Arg-Gln-Arg-Arg-Arg-Leu-Arg-Arg-Glu-Arg-Val-Arg-Ala-NH2 (SEQ ID NO: 22)

Fmoc Rink Amide MBHA resin was subjected to solid phase synthesis and purification by following the procedure in example 2 to yield 44 mg (3%). (ES)+-LCMS m/e calculated ("calcd") for $C_{181}H_{306}N_{70}O_{40}$. found 4102.86.

21. Synthesis of Ac-Lys-Arg-Tyr-Asp-Arg-Glu-Phe-Leu-Leu-Ala-Phe-Gln-Phe-Nle-Val-Tyr-Asp-Leu-Gly-Leu-Arg-Arg-Leu-Arg-Gln-Arg-Arg-Arg-Leu-Arg-Arg-Glu-Arg-Val-Arg-Ala-NH2 (SEQ ID NO: 23)

Fmoc Rink Amide MBHA resin (0.55 g, 0.25 mmol) was subjected to solid phase synthesis and purification by following the procedure in example 5 to yield 38.6 mg (3.3%). (ES)+-LCMS m/e calculated ("calcd") for $C_{211}H_{352}N_{76}O_{48}$. found 4721.59.

22. Synthesis of Ac-Ala-Arg-Val-Tyr-Asp-Leu-Gly-Leu-Arg-Arg-Leu-Arg-Gln-Arg-Arg-Arg-Leu-Arg-Arg-Glu-Arg-Val-Arg-Ala-Lys-Arg-Tyr-Asp-Arg-Glu-Phe-Leu-Leu-Ala-Phe-Gln-Phe-Nle-NH2 (SEQ ID NO: 24)

Fmoc Rink Amide MBHA resin (0.68 g, 0.25 mmol) was subjected to solid phase synthesis and purification by following the procedure in example 5 to yield 6 mg (0.5%). (ES)+-LCMS m/e calculated ("calcd") for $C_{220}H_{369}N_{81}O_{50}$. found 4948.85.

23. Synthesis of Ac-Gly-Ala-Ala-Glu-Ala-Ala-Ala-Tyr-Val-Tyr-Asp-Leu-Leu-Leu-Arg-Phe-Leu-Arg-Gln-Arg-Arg-Arg-Leu-Arg-Arg-Glu-Arg-Val-Arg-Ala-NH2 (SEQ ID NO: 25)

Fmoc Rink Amide MBHA resin (0.55 g, 0.25 mmol) was subjected to solid phase synthesis and purification by following the procedure in example 5 to yield 33 mg (3.6%). (ES)+-LCMS m/e calculated ("calcd") for $C_{160}H_{271}N_{59}O_{39}$. found 3645.27.

24. Synthesis of Ac-Gly-Ala-Ala-Glu-Ala-Ala-Ala-Arg-Val-Tyr-Asp-Leu-Gly-Leu-Arg-Arg-Leu-Arg-Gln-Arg-Arg-Tyr-Leu-Arg-Arg-Glu-Leu-Leu-Arg-Phe-NH2 (SEQ ID NO: 26)

Fmoc Rink Amide MBHA resin (0.73 g, 0.3 mmol) was subjected to solid phase synthesis and purification by following the procedure in example 5 to yield 21 mg (2.3%). (ES)+-LCMS m/e calculated ("calcd") for $C_{160}H_{271}N_{59}O_{39}$. found 3645.27.

25. Synthesis of Ac-Met-Ala-Ala-Leu-Ala-Tyr-Trp-Leu-Leu-Ala-Leu-Phe-Val-Tyr-Met-Trp-Thr-Asp-Leu-Leu-Leu-Phe-Lys-Lys-Arg-Pro-Lys-Pro-NH2 (SEQ ID NO: 27)

Fmoc Rink Amide MBHA resin was subjected to solid phase synthesis and purification by following the procedure in example 5. (ES)+-LCMS m/e calculated ("calcd") for $C_{171}H_{259}N_{37}O_{34}S_2$. found 3441.28.

26. Synthesis of Ac-Met-Ala-Ala-Leu-Ala-Tyr-Trp-Leu-Leu-Ala-Leu-Phe-Val-Tyr-Met-Trp-Thr-Asp-Leu-Nle-Leu-Phe-Lys-Lys-Arg-Pro-Lys-Pro-NH2 (SEQ ID NO: 28)

Fmoc Rink Amide MBHA resin was subjected to solid phase synthesis and purification by following the procedure in example 5. (ES)+-LCMS m/e calculated ("calcd") for $C_{171}H_{259}N_{37}O_{34}S_2$. found 3441.28.

27. Synthesis of Ac-Met-Ala-Lys-Leu-Lys-Tyr-Trp-Leu-Leu-Ala-Leu-Phe-Val-Tyr-Met-Trp-Thr-Asp-Leu-Nle-Leu-Phe-Lys-Lys-Arg-Pro-Lys-Pro-NH2 (SEQ ID NO: 29)

Fmoc Rink Amide MBHA resin was subjected to solid phase synthesis and purification by following the procedure in example 5. (ES)+-LCMS m/e calculated ("calcd") for $C_{177}H_{273}N_{39}O_{34}S_2$. found 3555.47.

28. Synthesis of Ac-Met-Ala-Lys-Leu-Lys-Tyr-Trp-Leu-Leu-Ala-Leu-Phe-Val-Tyr-Met-Trp-Thr-Asp-Leu-Leu-Leu-tBuAla-Lys-Lys-Arg-Pro-Lys-Pro-NH2 (SEQ ID NO: 30)

Fmoc Rink Amide MBHA resin was subjected to solid phase synthesis and purification by following the procedure in example 5. (ES)+-LCMS m/e calculated ("calcd") for $C_{175}H_{277}N_{39}O_{34}S_2$. found 3535.48.

29. Synthesis of Ac-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH 2 (SEQ ID NO: 31)

Fmoc Rink Amide MBHA resin was subjected to solid phase synthesis and purification by following the procedure in example 2 to yield 120 mg (1%). (ES)+-LCMS m/e calculated ("calcd") for $C_{160}H_{241}N_{37}O_{31}S$. found 3210.96.

30. Synthesis of Ac-Leu-Ala-Tyr-Trp-Leu-Leu-Ala-Leu-Phe-Val-Tyr-Met-Trp-Thr-Asp-Leu-Arg-Leu-t-Butyl-Ala-Lys-Lys-Arg-Pro-Lys-Pro-NH2 (SEQ ID NO: 32)

Fmoc Rink Amide MBHA resin was subjected to solid phase synthesis and purification by following the procedure in example 2 to yield 55 mg (6%). (ES)+-LCMS m/e calculated ("calcd") for $C_{158}H_{245}N_{37}O_{31}S$. found 3190.97.

31. Synthesis of Ac-Leu-Ala-Tyr-Trp-Leu-Leu-Ala-Leu-Phe-Val-Tyr-Met-Trp-Thr-Asp-Leu-Arg-Leu-Ala-Lys-Lys-Arg-Pro-Lys-Pro-NH2 (SEQ ID NO: 33)

Fmoc Rink Amide MBHA resin was subjected to solid phase synthesis and purification by following the procedure in example 2 to yield 46 mg (5%). (ES)+-LCMS m/e calculated ("calcd") for $C_{154}H_{237}N_{37}O_{31}S$. found 3134.86.

32. Synthesis of Ac-Ala-Asn-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 (SEQ ID NO: 34)

Fmoc Rink Amide MBHA resin was subjected to solid phase synthesis and purification by following the procedure in example 2 to yield 71 mg (7%). (ES)+-LCMS m/e calculated ("calcd") for $C_{167}H_{252}N_{40}O_{34}S$. found 3396.14.

33. Synthesis of Ac-Asn-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 (SEQ ID NO: 35)

Fmoc Rink Amide MBHA resin was subjected to solid phase synthesis and purification by following the procedure in example 2 to yield 93 mg (10%). (ES)+-LCMS m/e calculated ("calcd") for $C_{164}H_{247}N_{39}O_{33}S$. found 3325.06.

34. Synthesis of Ac-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 (SEQ ID NO: 36)

Fmoc Rink Amide MBHA resin was subjected to solid phase synthesis and purification by following the procedure in example 2 to yield 74 mg (8%). (ES)+-LCMS m/e calculated ("calcd") for $C_{154}H_{230}N_{36}O_{30}S$. found 3097.8.

35. Synthesis of Ac-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 (SEQ ID NO: 37)

Fmoc Rink Amide MBHA resin was subjected to solid phase synthesis and purification by following the procedure in example 2 to yield 60 mg (7%). (ES)+-LCMS m/e calculated ("calcd") for $C_{151}H_{225}N_{35}O_{29}S$. found 3026.72.

36. Synthesis of Ac-Met-Ala-Asn-Leu-Ala-Tyr-Trp-Leu-Leu-Ala-Leu-Phe-Val-Tyr-Leu-Trp-Thr-Asp-Leu-Arg-Leu-Phe-Lys-Lys-Arg-Pro-Lys-Pro-NH2 (SEQ ID NO: 38)

Fmoc Rink Amide MBHA resin was subjected to solid phase synthesis and purification by following the procedure in example 2 to yield 7.6 mg (1%). (ES)+-LCMS m/e calculated ("calcd") for $C_{173}H_{263}N_{41}O_{35}S$. found 3509.3.

37. Synthesis of Ac-Met-Ala-Asn-Leu-Ala-Tyr-Trp-Leu-Leu-Ala-Leu-Phe-Val-Tyr-Nle-Trp-Thr-Asp-Leu-Arg-Leu-Phe-Lys-Lys-Arg-Pro-Lys-Pro-NH2 (SEQ ID NO: 39)

Fmoc Rink Amide MBHA resin was subjected to solid phase synthesis and purification by following the procedure in example 2 to yield 9.7 mg (1%). (ES)+-LCMS m/e calculated ("calcd") for $C_{173}H_{263}N_{41}O_{35}S$. found 3509.3.

38. Synthesis of Ac-Met-Ala-Asn-Leu-Ala-Tyr-Trp-Leu-Leu-Ala-Leu-Phe-Val-Tyr-Lys-Trp-Thr-Asp-Leu-Arg-Leu-Phe-Lys-Lys-Arg-Pro-Lys-Pro-NH2 (SEQ ID NO: 40)

Fmoc Rink Amide MBHA resin was subjected to solid phase synthesis and purification by following the procedure in example 2 to yield 81.6 mg (8%). (ES)+-LCMS m/e calculated ("calcd") for $C_{174}H_{265}N_{41}O_{35}S$. found 3523.33.

39. Synthesis of Ac-Met-Ala-Asn-Leu-Ala-Tyr-Trp-Leu-Leu-Ala-Leu-Phe-Val-Tyr-Arg-Trp-Thr-Asp-Leu-Arg-Leu-Phe-Lys-Lys-Arg-Pro-Lys-Pro-NH2 (SEQ ID NO: 41)

Fmoc Rink Amide MBHA resin was subjected to solid phase synthesis and purification by following the procedure in example 2 to yield 81.6 mg (8%). (ES)+-LCMS m/e calculated ("calcd") for $C_{173}H_{264}N_{44}O_{35}S$. found 3552.33.

40. Synthesis of Ac-Met-Ala-Asn-Leu-Ala-Tyr-Trp-Leu-Leu-Ala-Leu-Phe-Val-Tyr-Met-Phe-Thr-Asp-Leu-Arg-Leu-Phe-Lys-Lys-Arg-Pro-Lys-Pro-NH2 (SEQ ID NO: 42)

Fmoc Rink Amide MBHA resin was subjected to solid phase synthesis and purification by following the procedure in example 2 to yield 48.7 mg (55%). (ES)+-LCMS m/e calculated ("calcd") for $C_{170}H_{260}N_{40}O_{35}S_2$. found 3488.3.

41. Synthesis of Ac-Met-Ala-Asn-Leu-Ala-Tyr-Trp-Leu-Leu-Ala-Leu-Phe-Val-Tyr-Met-1Nal-Thr-Asp-Leu-Arg-Leu-Phe-Lys-Lys-Arg-Pro-Lys-Pro-NH2 (SEQ ID NO: 43)

Fmoc Rink Amide MBHA resin was subjected to solid phase synthesis and purification by following the procedure in example 2 to yield 35.5 mg (3%). (ES)+-LCMS m/e calculated ("calcd") for $C_{174}H_{262}N_{40}O_{35}S_2$. found 3538.36.

42. Synthesis of Ac-Met-Ala-Asn-Leu-Ala-Tyr-Trp-Leu-Leu-Ala-Leu-Phe-Val-Tyr-Met-2Nal-Thr-Asp-Leu-Arg-Leu-Phe-Lys-Lys-Arg-Pro-Lys-Pro-NH2 (SEQ ID NO: 44)

Fmoc Rink Amide MBHA resin was subjected to solid phase synthesis and purification by following the procedure in example 2 to yield 24 mg (2%). (ES)+-LCMS m/e calculated ("calcd") for $C_{177}H_{262}N_{40}O_{35}S_2$. found 3538.36.

43. Synthesis of Ac-Met-Val-Lys-Tyr-Lys-Ile-Ala-Ser-Leu-Nle-Leu-Phe-Leu-Phe-Val-Ala-Met-Trp-Ser-Asp-Val-Ala-Leu-Ala-Lys-Lys-Arg-Pro-Lys-Pro-NH2 (SEQ ID NO: 45)

Fmoc Rink Amide MBHA resin was subjected to solid phase synthesis and purification by following the procedure in example 5. (ES)+-LCMS m/e calculated ("calcd") for $C_{169}H_{274}N_{40}O_{36}S_2$. found 3506.4.

44. Synthesis of Ac-Met-Tyr-Lys-Ser-Lys-Ile-Nle-Leu-Trp-Phe-Leu-Val-Leu-Phe-Val-Ala-Met-Trp-Ser-Asp-Val-Lys-Leu-Lys-Lys-Lys-Arg-Pro-Lys-Pro-NH2 (SEQ ID NO: 46)

Fmoc Rink Amide MBHA resin was subjected to solid phase synthesis and purification by following the procedure in example 5. (ES)+-LCMS m/e calculated ("calcd") for $C_{183}H_{293}N_{43}O_{36}S_2$. found 3735.72.

45. Synthesis of Ac-Met-Ala-Lys-Leu-Lys-Tyr-Trp-Leu-Leu-Ala-Leu-Phe-Val-Thr-Obzl-Met-Trp-Thr-Asp-Leu-Leu-Leu-tBuAla-Lys-Lys-Arg-Pro-NH2 (SEQ ID NO: 47)

Fmoc Rink Amide MBHA resin was subjected to solid phase synthesis and purification by following the procedure in example 2. (ES)+-LCMS m/e calculated ("calcd") for $C_{177}H_{281}N_{39}O_{34}S_2$. found 3563.54.

46. Synthesis of Ac-Met-Ala-Asn-Leu-Ala-Tyr-Trp-Leu-Leu-Ala-Leu-Phe-Val-Thr-Obzl-Tyr-Met-Trp-Thr-Asp-Leu-Arg-Leu-tBuAla-Lys-Lys-Arg-Pro-Lys-Pro-NH2 (SEQ ID NO: 48)

Fmoc Rink Amide MBHA resin was subjected to solid phase synthesis and purification by following the procedure in example 5. (ES)+-LCMS m/e calculated ("calcd") for $C_{172}H_{269}N_{41}O_{35}S_2$. found 3535.4.

47. Synthesis of Ac-Leu-Ala-Tyr-Trp-Leu-Leu-Ala-Leu-Phe-Val-Ala-Met-Trp-Thr-Asp-Leu-Arg-Leu-Phe-Lys-Lys-Arg-Pro-Lys-Pro-NH2 (SEQ ID NO: 49)

Fmoc Rink Amide MBHA resin was subjected to solid phase synthesis and purification by following the procedure in example 2 to yield 120 mg (13%) (ES)+-LCMS m/e calculated ("calcd") for $C_{154}H_{237}N_{37}O_{30}S$. found 3118.86.

48. Synthesis of Ac-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 (SEQ ID NO: 50)

Fmoc Rink Amide MBHA resin was subjected to solid phase synthesis and purification by following the procedure in example 2 to yield 96 mg (11%). (ES)+-LCMS m/e calculated ("calcd") for $C_{142}H_{216}N_{34}O_{27}S$. found 2863.55.

49. Synthesis of Ac-Leu-Leu-Ala-Leu-Phe-Val-Tyr-Met-Trp-Thr-Asp-Leu-Arg-Leu-Phe-Lys-Lys-Arg-Pro-Lys-Pro-NH2 (SEQ ID NO: 51)

Fmoc Rink Amide MBHA resin was subjected to solid phase synthesis and purification by following the procedure in example 2 to yield 137 mg (17%). (ES)+-LCMS m/e calculated ("calcd") for $C_{131}H_{206}N_{32}O_{26}S$. found 2677.33.

50. Synthesis of Ac-Lys-Gln-Tyr-Asp-Arg-Glu-Phe-Leu-Leu-Asp-Phe-Gln-Phe-Met-Pro-Ala-NH2 1:2 TFA (SEQ ID NO: 52)

Fmoc Rink Amide MBHA resin was subjected to solid phase synthesis and purification by following the procedure in example 5. (ES)+-LCMS m/e calculated ("calcd") for $C_{98}H_{141}N_{23}O_{26}S$. found 2089.39.

51. Synthesis of Ac-Lys-Gln-Tyr-Asp-Arg-Glu-Phe-Leu-Leu-Asp-Phe-Gln-Phe-Met-Pro-NH2 (SEQ ID NO: 53)

Fmoc Rink Amide MBHA resin was subjected to solid phase synthesis and purification by following the procedure in example 5. (ES)+-LCMS m/e calculated ("calcd") for $C_{95}H_{136}N_{22}O_{25}S$. found 2018.31.

52. Synthesis of Ac-Lys-Gln-Tyr-Asp-Arg-Glu-Phe-Leu-Leu-Asp-Phe-Gln-Phe-Met-NH2 (SEQ ID NO: 54)

Fmoc Rink Amide MBHA resin was subjected to solid phase synthesis and purification by following the procedure in example 5. (ES)+-LCMS m/e calculated ("calcd") for $C_{90}H_{129}N_{21}O_{24}S$. found 1921.2.

53. Synthesis of Ac-Lys-Gln-Tyr-Asp-Arg-Glu-Phe-Leu-Leu-Asp-Phe-Gln-Phe-NH2 (SEQ ID NO: 55)

Fmoc Rink Amide MBHA resin was subjected to solid phase synthesis and purification by following the procedure in example 5. (ES)+-LCMS m/e calculated ("calcd") for $C_{85}H_{120}N_{20}O_{23}$. found 1790.

54. Synthesis of Ac-Lys-Gln-Tyr-Asp-Arg-Glu-Phe-Leu-Leu-Asp-Phe-NH2 (SEQ ID NO: 56)

Fmoc Rink Amide MBHA resin was subjected to solid phase synthesis and purification by following the procedure in example 5. (ES)+-LCMS m/e calculated ("calcd") for $C_{71}H_{103}N_{17}O_{20}$. found 1514.69.

55. Synthesis of Ac-Lys-Gln-Tyr-Asp-Arg-Glu-Phe-Leu-Leu-Asp-Phe-Gln-Phe-Met-Ala-Ala-NH2 (SEQ ID NO: 57)

Fmoc Rink Amide MBHA resin was subjected to solid phase synthesis and purification by following the procedure in example 5. (ES)+-LCMS m/e calculated ("calcd") for $C_{96}H_{139}N_{23}O_{26}S$. found 2063.36.

56. Synthesis of Ac-Lys-Gln-Tyr-Asp-Arg-Glu-Phe-Leu-Leu-Asp-Phe-Gln-Phe-Ala-Pro-Ala-NH2 (SEQ ID NO: 58)

Fmoc Rink Amide MBHA resin was subjected to solid phase synthesis and purification by following the procedure in example 5. (ES)+-LCMS m/e calculated ("calcd") for $C_{96}H_{137}N_{23}O_{26}$. found 2029.27.

57. Synthesis of Ac-Lys-Gln-Tyr-Asp-Arg-Glu-Phe-Leu-Leu-Ala-Phe-Gln-Phe-Met-Pro-Ala-NH2 (SEQ ID NO: 59)

Fmoc Rink Amide MBHA resin was subjected to solid phase synthesis and purification by following the procedure in example 5. (ES)+-LCMS m/e calculated ("calcd") for $C_{97}H_{141}N_{23}O_{24}S$. found 2045.38.

58. Synthesis of Ac-Lys-Gln-Tyr-Asp-Arg-Ala-Phe-Leu-Leu-Asp-Phe-Gln-Phe-Met-Pro-Ala-NH2 (SEQ ID NO: 60)

Fmoc Rink Amide MBHA resin was subjected to solid phase synthesis and purification by following the procedure in example 5. (ES)+-LCMS m/e calculated ("calcd") for $C_{96}H_{139}N_{23}O_{24}S$. found 2031.36.

59. Synthesis of Ac-Lys-Gln-Tyr-Ala-Arg-Glu-Phe-Leu-Leu-Asp-Phe-Gln-Phe-Met-Pro-Ala-NH2 (SEQ ID NO: 61)

Fmoc Rink Amide MBHA resin was subjected to solid phase synthesis and purification by following the procedure in example 5. (ES)+-LCMS m/e calculated ("calcd") for $C_{97}H_{141}N_{23}O_{24}S$. found 2045.38.

60. Synthesis of Ac-Lys-Ala-Tyr-Asp-Arg-Glu-Phe-Leu-Leu-Asp-Phe-Gln-Phe-Met-Pro-Ala-NH2 (SEQ ID NO: 62)

Fmoc Rink Amide MBHA resin was subjected to solid phase synthesis and purification by following the procedure in example 5. (ES)+-LCMS m/e calculated ("calcd") for $C_{96}H_{138}N_{22}O_{25}S$. found 2032.34.

61. Synthesis of Ac-Ala-Gln-Tyr-Asp-Arg-Glu-Phe-Leu-Leu-Asp-Phe-Gln-Phe-Met-Pro-Ala-NH2 (SEQ ID NO: 63)

Fmoc Rink Amide MBHA resin was subjected to solid phase synthesis and purification by following the procedure in example 5. (ES)+-LCMS m/e calculated ("calcd") for $C_{95}H_{134}N_{22}O_{26}S$. found 2032.3.

62. Synthesis of Ac-Lys-Gln-Tyr-Asp-Arg-Glu-Phe-Leu-Leu-Asp-Phe-Gln-Phe-Met-Pro-(D)Ala-NH2 (SEQ ID NO: 64)

Fmoc Rink Amide MBHA resin was subjected to solid phase synthesis and purification by following the procedure in example 5. (ES)+-LCMS m/e calculated ("calcd") for $C_{98}H_{141}N_{23}O_{26}S$. found 2089.39.

63. Synthesis of Ac-Lys-Gln-Tyr-Asp-Arg-Glu-Phe-Leu-Leu-Asp-Phe-Gln-Phe-Met-(D)Pro-Ala-NH2 (SEQ ID NO: 65)

Fmoc Rink Amide MBHA resin was subjected to solid phase synthesis and purification by following the procedure in example 5. (ES)+-LCMS m/e calculated ("calcd") for $C_{98}H_{141}N_{23}O_{26}S$. found 2089.39.

64. Synthesis of Ac-Lys-Gln-Tyr-Asp-Arg-Glu-Phe-Leu-Leu-Asp-Phe-Gln-Phe-(D)Met-Pro-Ala-NH2 (SEQ ID NO: 66)

Fmoc Rink Amide MBHA resin was subjected to solid phase synthesis and purification by following the procedure in example 5. (ES)+-LCMS m/e calculated ("calcd") for $C_{98}H_{141}N_{23}O_{26}S$. found 2089.39.

65. Synthesis of Ac-Lys-Gln-Tyr-Asp-Arg-Glu-Phe-Leu-Leu-Asp-Phe-Gln-(D)Phe-Met-Pro-Ala-NH2 (SEQ ID NO: 67)

Fmoc Rink Amide MBHA resin was subjected to solid phase synthesis and purification by following the procedure in example 5. (ES)+-LCMS m/e calculated ("calcd") for $C_{98}H_{141}N_{23}O_{26}S$. found 2089.39.

66. Synthesis of Ac-Tyr-Asp-Arg-Glu-Phe-Leu-Leu-Asp-Phe-Gln-Phe-Met-NH2 (SEQ ID NO: 68)

Fmoc Rink Amide MBHA resin was subjected to solid phase synthesis and purification by following the procedure in example 2 to yield 5 mg (1%). (ES)+-LCMS m/e calculated ("calcd") for $C_{79}H_{109}N_{17}O_{21}S$. found 1664.89.

67. Synthesis of Ac-Tyr-Asp-Arg-Glu-Phe-Leu-Leu-Asp-Phe-Gln-Phe-NH2 (SEQ ID NO: 69)

Fmoc Rink Amide MBHA resin was subjected to solid phase synthesis and purification by following the procedure in example 2 to yield 69 mg (17%). (ES)+-LCMS m/e calculated ("calcd") for $C_{74}H_{100}N_{16}O_{20}$. found 1533.7.

68. Synthesis of Ac-Tyr-Asp-Arg-Glu-Phe-Leu-Leu-Asp-Phe-Gln-Phe-Nle-NH2 (SEQ ID NO: 70)

Fmoc Rink Amide MBHA resin was subjected to solid phase synthesis and purification by following the procedure in example 2 to yield 128 mg (29%). (ES)+-LCMS m/e calculated ("calcd") for $C_{80}H_{111}N_{17}O_{21}$. found 1646.85.

69. Synthesis of Ac-Tyr-Asp-Arg-Gln-Phe-Leu-Leu-Asp-Phe-Gln-Phe-Nle-NH2 (SEQ ID NO: 71)

Fmoc Rink Amide MBHA resin was subjected to solid phase synthesis and purification by following the procedure in example 2 to yield 157 mg (35%). (ES)+-LCMS m/e calculated ("calcd") for $C_{80}H_{112}N_{18}O_{20}$. found 1645.87.

70. Synthesis of Ac-Tyr-Asp-Arg-Glu-Phe-Leu-Leu-Ala-Phe-Gln-Phe-Nle-NH2 (SEQ ID NO: 72)

Fmoc Rink Amide MBHA resin was subjected to solid phase synthesis and purification by following the procedure in example 2 to yield 145.5 mg (34%). (ES)+-LCMS m/e calculated ("calcd") for $C_{79}H_{111}N_{17}O_{19}$. found 1602.85.

71. Synthesis of Ac-Tyr-Asp-Arg-Glu-Phe-Leu-Leu-Aib-Phe-Gln-Phe-Nle-NH2 (SEQ ID NO: 73)

Fmoc Rink Amide MBHA resin was subjected to solid phase synthesis and purification by following the procedure in example 2 to yield 64 mg (15%). (ES)+-LCMS m/e calculated ("calcd") for $C_{80}H_{113}N_{17}O_{19}$. found 1616.87.

72. Synthesis of Ac-Tyr-Asn-Arg-Glu-Phe-Leu-Leu-Asp-Phe-Gln-Phe-Nle-NH2 (SEQ ID NO: 74)

Fmoc Rink Amide MBHA resin was subjected to solid phase synthesis and purification by following the procedure in example 2 to yield 18 mg (3%). (ES)+-LCMS m/e calculated ("calcd") for $C_{80}H_{112}N_{18}O_{20}$. found 1645.87.

73. Synthesis of Ac-Tyr-Asn-Arg-Gln-Phe-Leu-Leu-Asp-Phe-Gln-Phe-Nle-NH2 (SEQ ID NO: 75)

Fmoc Rink Amide MBHA resin was subjected to solid phase synthesis and purification by following the procedure in example 2 to yield 9 mg (2%). (ES)+-LCMS m/e calculated ("calcd") for $C_{80}H_{113}N_{19}O_{19}$. found 1644.89.

74. Synthesis of Ac-Tyr-Mamb-Leu-Leu-Ala-Phe-Gln-Phe-Nle-NH2 (SEQ ID NO: 76)

Fmoc Rink Amide MBHA resin was subjected to solid phase synthesis and purification by following the procedure in example 2. (ES)+-LCMS m/e calculated ("calcd") for $C_{63}H_{85}N_{11}O_{12}$. found 1188.43.

75. Synthesis of Ac-Tyr-Mamp-Leu-Leu-Ala-Phe-Gln-Phe-Nle-NH2 (SEQ ID NO: 77)

Fmoc Rink Amide MBHA resin was subjected to solid phase synthesis and purification by following the procedure in example 2. (ES)+-LCMS m/e calculated ("calcd") for $C_{64}H_{87}N_{11}O_{12}$. found 1202.46.

76. Synthesis of Ac-Tyr-NVa-Leu-Leu-Ala-Phe-Gln-Phe-Nle-NH2 (SEQ ID NO: 78)

Fmoc Rink Amide MBHA resin was subjected to solid phase synthesis and purification by following the procedure in example 2. (ES)+-LCMS m/e calculated ("calcd") for $C_{60}H_{87}N_{11}O_{12}$. found 1154.41.

77. Synthesis of Ac-Phe-5Ava-Leu-Leu-Ala-Phe-Gln-Phe-Nle-NH2 (SEQ ID NO: 79)

Fmoc Rink Amide MBHA resin was subjected to solid phase synthesis and purification by following the procedure in example 2. (ES)+-LCMS m/e calculated ("calcd") for $C_{60}H_{87}N_{11}O_{11}$. found 1138.41.

78. Synthesis of Ac-Lys-Arg-Tyr-Asp-Arg-Glu-Phe-Leu-Leu-Ala-Phe-Gln-Phe-Nle-NH2 (SEQ ID NO: 80)

Fmoc Rink Amide MBHA resin was subjected to solid phase synthesis and purification by following the procedure in example 2 to yield 60 mg (12%). (ES)+-LCMS m/e calculated ("calcd") for $C_{91}H_{135}N_{23}O_{21}$. found 1887.21.

79. Synthesis of Ac-Gln-Tyr-Asp-Arg-Glu-Phe-Leu-Leu-Asp-Phe-Gln-Phe-Met-Pro-Ala-NH2 (SEQ ID NO: 81)

Fmoc Rink Amide MBHA resin was subjected to solid phase synthesis and purification by following the procedure in example 5. (ES)+-LCMS m/e calculated ("calcd") for $C_{92}H_{129}N_{21}O_{25}S$. found 1961.22.

80. Synthesis of Ac-Tyr-Asp-Arg-Glu-Phe-Leu-Leu-Asp-Phe-Gln-Phe-Met-Pro-Ala-NH2 (SEQ ID NO: 82)

Fmoc Rink Amide MBHA resin was subjected to solid phase synthesis and purification by following the procedure in example 5. (ES)+-LCMS m/e calculated ("calcd") for $C_{87}H_{121}N_{19}O_{23}S$. found 1833.09.

81. Synthesis of Ac-(D)Lys-Gln-Tyr-Asp-Arg-Glu-Phe-Leu-Leu-Asp-Phe-Gln-Phe-Met-Pro-Ala-NH2 (SEQ ID NO: 83)

Fmoc Rink Amide MBHA resin was subjected to solid phase synthesis and purification by following the procedure in example 5. (ES)+-LCMS m/e calculated ("calcd") for $C_{98}H_{141}N_{23}O_{26}S$. found 2089.39.

82. Synthesis of Ac-Lys-Arg-Phe-Asp-Arg-Glu-Phe-Leu-Leu-Ala-Phe-Gln-Phe-Nle-NH2 (SEQ ID NO: 84)

Fmoc Rink Amide MBHA resin was subjected to solid phase synthesis and purification by following the procedure in example 2 to yield 64 mg (11%). (ES)+-LCMS m/e calculated ("calcd") for $C_{91}H_{135}N_{23}O_{20}$. found 1871.21.

83. Synthesis of Ac-Lys-Arg-Lys-Arg-Phe-Asp-Arg-Glu-Phe-Leu-Leu-Ala-Phe-Gln-Phe-Nle-NH2 (SEQ ID NO: 85)

Fmoc Rink Amide MBHA resin was subjected to solid phase synthesis and purification by following the procedure in example 2. (ES)+-LCMS m/e calculated ("calcd") for $C_{103}H_{159}N_{29}O_{22}$. found 2155.57.

Example 84

Tables and lists of other exemplary peptides of the invention with measured IC50 with regard to binding to eIF4E, as well as other exemplary cell-penetrating peptides of the invention with measured IC50 with regard to binding to eIF4E.

TABLE 1

-Peptides which bind eIF4E but are not cell-penetrating

| SEQ N | SEQUENCE 3-LETTER CODE | IC50 (µM) |
|---|---|---|
| 52 | Ac-Lys-Gln-Tyr-Asp-Arg-Glu-Phe-Leu-Leu-Asp-Phe-Gln-Phe-Met-Pro-Ala-NH2 | 10.45 |
| 53 | Ac-Lys-Gln-Tyr-Asp-Arg-Glu-Phe-Leu-Leu-Asp-Phe-Gln-Phe-Met-Pro-NH2 | 7.456 |
| 54 | Ac-Lys-Gln-Tyr-Asp-Arg-Glu-Phe-Leu-Leu-Asp-Phe-Gln-Phe-Met-NH2 | 8.835 |
| 55 | Ac-Lys-Gln-Tyr-Asp-Arg-Glu-Phe-Leu-Leu-Asp-Phe-Gln-Phe-NH2 | 14.58 |
| 56 | Ac-Lys-Gln-Tyr-Asp-Arg-Glu-Phe-Leu-Leu-Asp-Phe-NH2 | 3.439 |
| 57 | Ac-Lys-Gln-Tyr-Asp-Arg-Glu-Phe-Leu-Leu-Asp-Phe-Gln-Phe-Met-Ala-Ala-NH2 | 6.964 |
| 58 | Ac-Lys-Gln-Tyr-Asp-Arg-Glu-Phe-Leu-Leu-Asp-Phe-Gln-Phe-Ala-Pro-Ala-NH2 | 11.33 |
| 59 | Ac-Lys-Gln-Tyr-Asp-Arg-Glu-Phe-Leu-Leu-Ala-Phe-Gln-Phe-Met-Pro-Ala-NH2 | 1.416 |
| 60 | Ac-Lys-Gln-Tyr-Asp-Arg-Ala-Phe-Leu-Leu-Asp-Phe-Gln-Phe-Met-Pro-Ala-NH2 | 9.257 |
| 61 | Ac-Lys-Gln-Tyr-Ala-Arg-Glu-Phe-Leu-Leu-Asp-Phe-Gln-Phe-Met-Pro-Ala-NH2 | 11.77 |
| 62 | Ac-Lys-Ala-Tyr-Asp-Arg-Glu-Phe-Leu-Leu-Asp-Phe-Gln-Phe-Met-Pro-Ala-NH2 | 13.57 |
| 63 | Ac-Ala-Gln-Tyr-Asp-Arg-Glu-Phe-Leu-Leu-Asp-Phe-Gln-Phe-Met-Pro-Ala-NH2 | 12.29 |
| 64 | Ac-Lys-Gln-Tyr-Asp-Arg-Glu-Phe-Leu-Leu-Asp-Phe-Gln-Phe-Met-Pro-(D)Ala-NH2 | 8.687 |
| 65 | Ac-Lys-Gln-Tyr-Asp-Arg-Glu-Phe-Leu-Leu-Asp-Phe-Gln-Phe-Met-(D)Pro-Ala-NH2 | 7.691 |
| 66 | Ac-Lys-Gln-Tyr-Asp-Arg-Glu-Phe-Leu-Leu-Asp-Phe-Gln-Phe-(D)Met-Pro-Ala-NH2 | 7.749 |
| 67 | Ac-Lys-Gln-Tyr-Asp-Arg-Glu-Phe-Leu-Leu-Asp-Phe-Gln-(D)Phe-Met-Pro-Ala-NH2 | 13.69 |
| 68 | Ac-Tyr-Asp-Arg-Glu-Phe-Leu-Leu-Asp-Phe-Gln-Phe-Met-NH2 | 13.09 |
| 69 | Ac-Tyr-Asp-Arg-Glu-Phe-Leu-Leu-Asp-Phe-Gln-Phe-NH2 | 12.43 |
| 70 | Ac-Tyr-Asp-Arg-Glu-Phe-Leu-Leu-Asp-Phe-Gln-Phe-Nle-NH2 | 3.393 |
| 71 | Ac-Tyr-Asp-Arg-Gln-Phe-Leu-Leu-Asp-Phe-Gln-Phe-Nle-NH2 | 10.97 |
| 72 | Ac-Tyr-Asp-Arg-Glu-Phe-Leu-Leu-Ala-Phe-Gln-Phe-Nle-NH2 | 2.696 |
| 73 | Ac-Tyr-Asp-Arg-Glu-Phe-Leu-Leu-Aib-Phe-Gln-Phe-Nle-NH2 | 3.56 |
| 74 | Ac-Tyr-Asn-Arg-Glu-Phe-Leu-Leu-Asp-Phe-Gln-Phe-Nle-NH2 | 10.88 |
| 75 | Ac-Tyr-Asn-Arg-Gln-Phe-Leu-Leu-Asp-Phe-Gln-Phe-Nle-NH2 | 10.97 |

TABLE 1-continued

Peptides which bind eIF4E but are not cell-penetrating

| SEQ N | SEQUENCE 3-LETTER CODE | IC50 (µM) |
|---|---|---|
| 76 | Ac-Tyr-Mamb-Leu-Leu-Ala-Phe-Gln-Phe-Nle-NH2 | 12.01 |
| 77 | Ac-Tyr-Mamp-Leu-Leu-Ala-Phe-Gln-Phe-Nle-NH2 | 5.348 |
| 78 | Ac-Tyr-NVa-Leu-Leu-Ala-Phe-Gln-Phe-Nle-NH2 | 6.627 |
| 79 | Ac-Phe-5Ava-Leu-Leu-Ala-Phe-Gln-Phe-Nle-NH2 | 9.34 |
| 80 | Ac-Lys-Arg-Tyr-Asp-Arg-Glu-Phe-Leu-Leu-Ala-Phe-Gln-Phe-Nle-NH2 | 0.643 |
| 81 | Ac-Gln-Tyr-Asp-Arg-Glu-Phe-Leu-Leu-Asp-Phe-Gln-Phe-Met-Pro-Ala-NH2 | 8.675 |
| 82 | Ac-Tyr-Asp-Arg-Glu-Phe-Leu-Leu-Asp-Phe-Gln-Phe-Met-Pro-Ala-NH2 | 7.517 |
| 83 | Ac-(D)Lys-Gln-Tyr-Asp-Arg-Glu-Phe-Leu-Leu-Asp-Phe-Gln-Phe-Met-Pro-Ala-NH2 | 1.669 |
| 84 | Ac-Lys-Arg-Phe-Asp-Arg-Glu-Phe-Leu-Leu-Ala-Phe-Gln-Phe-Nle-NH2 | 4.065 |
| 85 | Ac-Lys-Arg-Lys-Arg-Phe-Asp-Arg-Glu-Phe-Leu-Leu-Ala-Phe-Gln-Phe-Nle-NH2 | 0.32 |

TABLE 2

Cell-penetrating peptides with the Y----LL-F motif (SEQ ID NO: 90)

| SEQ N | SEQUENCE 3-LETTER CODE | IC50 (µM) |
|---|---|---|
| 7 | Ac-Lys-Arg-Tyr-Asp-Arg-Glu-Phe-Leu-Leu-Ala-Phe-Gln-Phe-Nle-Val-Tyr-Asp-Leu-Gly-Leu-Arg-Arg-Leu-Arg-Gln-Arg-Arg-Leu-Arg-Arg-NH2 | 0.21 |
| 12 | Ac-Met-Val-Lys-Tyr-Lys-Ile-Gly-Ser-Leu-Leu-Leu-Phe-Leu-Phe-Val-Ala-Met-Trp-Ser-Asp-Val-Gly-Leu-Cys-Lys-Lys-Arg-Pro-Lys-Pro-NH2 | 4.128 |
| 13 | Ac-Met-Val-Lys-Ser-Lys-Tyr-Gly-Ser-Trp-Ile-Leu-Leu-Leu-Phe-Val-Ala-Met-Trp-Ser-Asp-Val-Gly-Leu-Cys-Lys-Lys-Arg-Pro-Lys-Pro-NH2 | 6.893 |
| 14 | Ac-Met-Tyr-Lys-Ser-Lys-Ile-Leu-Leu-Trp-Phe-Leu-Val-Leu-Phe-Val-Ala-Met-Trp-Ser-Asp-Val-Gly-Leu-Cys-Lys-Lys-Arg-Pro-Lys-Pro-NH2 | 3.623 |
| 15 | Ac-Met-Val-Lys-Ser-Lys-Ile-Tyr-Ser-Trp-Ile-Leu-Leu-Leu-Phe-Phe-Ala-Met-Trp-Ser-Asp-Val-Gly-Leu-Cys-Lys-Lys-Arg-Pro-Lys-Pro-NH2 | 5.2 |
| 16 | Ac-Met-Ala-Asn-Leu-Gly-Tyr-Trp-Leu-Leu-Ala-Leu-Phe-Val-Tyr-Met-Trp-Thr-Asp-Leu-Leu-Leu-Phe-Lys-Lys-Arg-Pro-Lys-Pro-NH2 | 3.03 |
| 17 | Ac-Met-Val-Lys-Tyr-Lys-Ile-Ala-Ser-Leu-Leu-Leu-Phe-Leu-Phe-Val-Ala-Met-Trp-Ser-Asp-Val-Ala-Leu-Ala-Lys-Lys-Arg-Pro-Lys-Pro-NH2 | 12.47 |
| 18 | Ac-Met-Val-Lys-Tyr-Lys-Ile-Ala-Ser-Leu-Leu-Leu-Phe-Leu-Phe-Val-Ala-Met-Trp-Ser-Asp-Val-Lys-Leu-Lys-Lys-Lys-Arg-Pro-Lys-Pro-NH2 | 6.707 |
| 19 | Ac-Met-Tyr-Lys-Ser-Lys-Ile-Leu-Leu-Trp-Phe-Leu-Val-Leu-Phe-Val-Ala-Met-Trp-Ser-Asp-Val-Ala-Leu-Ala-Lys-Lys-Arg-Pro-Lys-Pro-NH2 | 7.209 |

TABLE 2-continued

Cell-penetrating peptides with the Y----LL-F motif
(SEQ ID NO: 90)

| SEQ N | SEQUENCE 3-LETTER CODE | IC50 (µM) |
|---|---|---|
| 20 | Ac-Met-Val-Lys-Ser-Lys-Ile-Tyr-Ser-Trp-Ile-Leu-Leu-Leu-Phe-Phe-Ala-Met-Trp-Ser-Asp-Val-Ala-Leu-Ala-Lys-Lys-Arg-Pro-Lys-Pro-NH2 | 9.958 |
| 21 | Ac-Met-Val-Lys-Ser-Lys-Ile-Tyr-Ser-Trp-Ile-Leu-Leu-Leu-Phe-Phe-Ala-Met-Trp-Ser-Asp-Val-Lys-Leu-Lys-Lys-Lys-Arg-Pro-Lys-Pro-NH2 | 6.854 |
| 22 | Ac-Lys-Arg-Tyr-Asp-Arg-Glu-Phe-Leu-Leu-Ala-Phe-Gln-Phe-Nle-Arg-Arg-Leu-Arg-Gln-Arg-Arg-Leu-Arg-Arg-Glu-Arg-Val-Arg-Ala-NH2 | 0.198 |
| 23 | Ac-Lys-Arg-Tyr-Asp-Arg-Glu-Phe-Leu-Leu-Ala-Phe-Gln-Phe-Nle-Val-Tyr-Asp-Leu-Gly-Leu-Arg-Arg-Leu-Arg-Gln-Arg-Arg-Arg-Leu-Arg-Arg-Glu-Arg-Val-Arg-Ala-NH2 | 0.18 |
| 24 | Ac-Ala-Arg-Val-Tyr-Asp-Leu-Gly-Leu-Arg-Arg-Leu-Arg-Gln-Arg-Arg-Arg-Leu-Arg-Arg-Glu-Arg-Val-Arg-Ala-Lys-Arg-Tyr-Asp-Arg-Glu-Phe-Leu-Leu-Ala-Phe-Gln-Phe-Nle-NH2 | 0.019 |
| 25 | Ac-Gly-Ala-Ala-Glu-Ala-Ala-Ala-Tyr-Val-Tyr-Asp-Leu-Leu-Leu-Arg-Phe-Leu-Arg-Gln-Arg-Arg-Arg-Leu-Arg-Arg-Glu-Arg-Val-Arg-Ala-NH2 | 10.98 |
| 26 | Ac-Gly-Ala-Ala-Glu-Ala-Ala-Ala-Arg-Val-Tyr-Asp-Leu-Gly-Leu-Arg-Arg-Leu-Arg-Gln-Arg-Arg-Tyr-Leu-Arg-Arg-Glu-Leu-Leu-Arg-Phe-NH2 | 0.25 |

TABLE 2a

Cell penetrating peptides with the Y----LL-F motif (SEQ ID NO: 90)
and the YWLLALFVY motif (SEQ ID NO: 2)

| SEQ N | SEQUENCE 3-LETTER CODE | IC50 (µM) |
|---|---|---|
| 9 | Ac-Met-Ala-Lys-Leu-Lys-Tyr-Trp-Leu-Leu-Ala-Leu-Phe-Val-Tyr-Met-Trp-Thr-Asp-Leu-Leu-Leu-Phe-Lys-Lys-Arg-Pro-Lys-Pro-NH2 | 4.404 |
| 10 | Ac-Met-Ala-Asn-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 | 1.703 |
| 11 | Ac-Met-Ala-Asn-Leu-Ala-Tyr-Trp-Leu-Leu-Ala-Leu-Phe-Val-Tyr-Met-Trp-Thr-Asp-Leu-Arg-Leu-tBuAla-Lys-Lys-Arg-Pro-Lys-Pro-NH2 | 2.372 |
| 27 | Ac-Met-Ala-Ala-Leu-Ala-Tyr-Trp-Leu-Leu-Ala-Leu-Phe-Val-Tyr-Met-Trp-Thr-Asp-Leu-Leu-Leu-Phe-Lys-Lys-Arg-Pro-Lys-Pro-NH2 | 10.66 |
| 28 | Ac-Met-Ala-Ala-Leu-Ala-Tyr-Trp-Leu-Leu-Ala-Leu-Phe-Val-Tyr-Met-Trp-Thr-Asp-Leu-Nle-Leu-Phe-Lys-Lys-Arg-Pro-Lys-Pro-NH2 | 4.589 |
| 29 | Ac-Met-Ala-Lys-Leu-Lys-Tyr-Trp-Leu-Leu-Ala-Leu-Phe-Val-Tyr-Met-Trp-Thr-Asp-Leu-Nle-Leu-Phe-Lys-Lys-Arg-Pro-Lys-Pro-NH2 | 7.388 |
| 30 | Ac-Met-Ala-Lys-Leu-Lys-Tyr-Trp-Leu-Leu-Ala-Leu-Phe-Val-Tyr-Met-Trp-Thr-Asp-Leu-Leu-Leu-tBuAla-Lys-Lys-Arg-Pro-Lys-Pro-NH2 | 2.237 |
| 31 | Ac-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 | 4.349 |
| 32 | Ac-Leu-Ala-Tyr-Trp-Leu-Leu-Ala-Leu-Phe-Val-Tyr-Met-Trp-Thr-Asp-Leu-Arg-Leu-t-Butyl-Ala-Lys-Lys-Arg-Pro-Lys-Pro-NH2 | 4.733 |

TABLE 2a-continued

Cell penetrating peptides with the Y----LL-F motif (SEQ ID NO: 90) and the YWLLALFVY motif (SEQ ID NO: 2)

| SEQ N | SEQUENCE 3-LETTER CODE | IC50 (µM) |
|---|---|---|
| 33 | Ac-Leu-Ala-Tyr-Trp-Leu-Leu-Ala-Leu-Phe-Val-Tyr-Met-Trp-Thr-Asp-Leu-Arg-Leu-Ala-Lys-Lys-Arg-Pro-Lys-Pro-NH2 | 6.239 |
| 34 | Ac-Ala-Asn-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 | 2.219 |
| 35 | Ac-Asn-Leu-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 | 5.044 |
| 36 | Ac-Ala-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 | 2.534 |
| 37 | Ac-Tyr-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 | 2.904 |
| 38 | Ac-Met-Ala-Asn-Leu-Ala-Tyr-Trp-Leu-Leu-Ala-Leu-Phe-Val-Tyr-Leu-Trp-Thr-Asp-Leu-Arg-Leu-Phe-Lys-Lys-Arg-Pro-Lys-Pro-NH2 | 3.042 |
| 39 | Ac-Met-Ala-Asn-Leu-Ala-Tyr-Trp-Leu-Leu-Ala-Leu-Phe-Val-Tyr-Nle-Trp-Thr-Asp-Leu-Arg-Leu-Phe-Lys-Lys-Arg-Pro-Lys-Pro-NH2 | 1.751 |
| 40 | Ac-Met-Ala-Asn-Leu-Ala-Tyr-Trp-Leu-Leu-Ala-Leu-Phe-Val-Tyr-Lys-Trp-Thr-Asp-Leu-Arg-Leu-Phe-Lys-Lys-Arg-Pro-Lys-Pro-NH2 | -3.607 |
| 41 | Ac-Met-Ala-Asn-Leu-Ala-Tyr-Trp-Leu-Leu-Ala-Leu-Phe-Val-Tyr-Arg-Trp-Thr-Asp-Leu-Arg-Leu-Phe-Lys-Lys-Arg-Pro-Lys-Pro-NH2 | 3.481 |
| 42 | Ac-Met-Ala-Asn-Leu-Ala-Tyr-Trp-Leu-Leu-Ala-Leu-Phe-Val-Tyr-Met-Phe-Thr-Asp-Leu-Arg-Leu-Phe-Lys-Lys-Arg-Pro-Lys-Pro-NH2 | 3.912 |
| 43 | Ac-Met-Ala-Asn-Leu-Ala-Tyr-Trp-Leu-Leu-Ala-Leu-Phe-Val-Tyr-Met-1Nal-Thr-Asp-Leu-Arg-Leu-Phe-Lys-Lys-Arg-Pro-Lys-Pro-NH2 | 2.593 |
| 44 | Ac-Met-Ala-Asn-Leu-Ala-Tyr-Trp-Leu-Leu-Ala-Leu-Phe-Val-Tyr-Met-2Nal-Thr-Asp-Leu-Arg-Leu-Phe-Lys-Lys-Arg-Pro-Lys-Pro-NH2 | 2.15 |

TABLE 3 cell-penetrating peptides without the Y----LL-F motif (SEQ ID NO: 90)

| SEQ N | SEQUENCE 3-LETTER CODE | IC50 (µM) |
|---|---|---|
| 45 | Ac-Met-Val-Lys-Tyr-Lys-Ile-Ala-Ser-Leu-Nle-Leu-Phe-Leu-Phe-Val-Ala-Met-Trp-Ser-Asp-Val-Ala-Leu-Ala-Lys-Lys-Arg-Pro-Lys-Pro-NH2 | 3.062 |
| 46 | Ac-Met-Tyr-Lys-Ser-Lys-Ile-Nle-Leu-Trp-Phe-Leu-Val-Leu-Phe-Val-Ala-Met-Trp-Ser-Asp-Val-Lys-Leu-Lys-Lys-Lys-Arg-Pro-Lys-Pro-NH2 | 6.375 |
| 47 | Ac-Met-Ala-Lys-Leu-Lys-Tyr-Trp-Leu-Leu-Ala-Leu-Phe-Val-Thr-Obzl-Met-Trp-Thr-Asp-Leu-Leu-Leu-tBuAla-Lys-Lys-Arg-Pro-NH2 | 5.314 |
| 48 | Ac-Met-Ala-Asn-Leu-Ala-Tyr-Trp-Leu-Leu-Ala-Leu-Phe-Val-Thr-Obzl-Tyr-Met-Trp-Thr-Asp-Leu-Arg-Leu-tBuAla-Lys-Lys-Arg-Pro-Lys-Pro-NH2 | 3.402 |

TABLE 3-continued cell-penetrating peptides without the
Y----LL-F motif (SEQ ID NO: 90)

| SEQ N | SEQUENCE 3-LETTER CODE | IC50 (µM) |
|---|---|---|
| 49 | Ac-Leu-Ala-Tyr-Trp-Leu-Leu-Ala-Leu-Phe-Val-Ala-Met-Trp-Thr-Asp-Leu-Arg-Leu-Phe-Lys-Lys-Arg-Pro-Lys-Pro-NH2 | 1.985 |
| 50 | Ac-Trp-Leu-Leu-Ala-Leu-Phe-Val-Tyr-Met-Trp-Thr-Asp-Leu-Arg-Leu-Phe-Lys-Lys-Arg-Pro-Lys-Pro-NH2 | 2.36 |
| 51 | Ac-Leu-Leu-Ala-Leu-Phe-Val-Tyr-Met-Trp-Thr-Asp-Leu-Arg-Leu-Phe-Lys-Lys-Arg-Pro-Lys-Pro-NH2 | 3.747 |

Full-Length eif4E Sequence (SEQ ID NO 86)

MATVEPETTPTPNPPTTEEEKTESNQEVANPEHYIKHPLQNRWALWFFKN
DKSKTWQANLRLISKFDTVEDFWALYNHIQLSSNLMPGCDYSLFKDGIEP

-continued
MWEDEKNKRGGRWLITLNKQQRRSDLDRFWLETLLCLIGESFDDYSDDVC
GAVVNVRAKGDKIAIWTTECENREAVTHIGRVYKERLGLPPKIVIGYQSH
ADTATKSGSTTKNRFVV Eif4e Sequence 28-217 (SEQ ID NO: 87)

```
                10         20         30         40         50         60
                           VAN PEHYIKHPLQ NRWALWFFKN DKSKTWQANL
                70         80         90        100        110        120
        RLISKFDTVE DFWALYNHIQ LSSNLMPGCD YSLFKDGIEP MWEDEKNKRG GRWLITLNKQ
               130        140        150        160        170        180
        QRRSDLDRFW LETLLCLIGE SFDDYSDDVC GAVVNVRAKG DKIAINTTEC ENREAVTHIG
               190        200        210
        RVYKERLGLP PKIVIGYQSH ADTATKSGST TKNRFVV
```

The invention claimed is:

1. A cell-penetrating peptide which binds mammalian initiation factor eIF4E (CPP-eIF4E), wherein the peptide comprises an amino acid sequence selected from the group consisting of SEQ ID NOS: 7, 9-11, 12-26, 27-44 and 45-51.

2. The cell-penetrating peptide of claim 1, wherein the amino acid sequence is at least 9 to about 40 amino acids and wherein further the mammalian initiation factor eIF4E is human initiation factor eIF4E.

3. The cell-penetrating peptide of claim 1, wherein the peptide comprises an amino acid sequence of SEQ ID NOS: 7, 9 and 10-44, wherein said amino acid sequence further comprises, in part, an amino acid sequence motif selected from the group consisting of:
   a) YxxxxzzxF (SEQ ID NO: 1), wherein Y is tyrosine (Tyr), x is any amino acid, z is leucine (Leu) or norleucine (Nle), and F is phenylalanine (Phe), or
   b) Tyr-Trp-Leu-Leu-Ala-Leu-Phe-Val-Tyr (SEQ ID NO: 2).

4. The cell-penetrating peptide of claim 3, wherein the amino acid sequence is at least 9 to about 40 amino acids and wherein further the mammalian initiation factor eIF4E is human initiation factor eIF4E.

5. The cell-penetrating peptide of claim 4, wherein the peptide comprises an amino acid sequence selected from the group consisting of SEQ ID NOS: 7, 12 and 13-26 and wherein further the amino acid sequence motif is YxxxxzzxF (SEQ ID NO: 90), wherein Y is tyrosine (Tyr), x is any amino acid, z is leucine (Leu), and F is phenylalanine (Phe).

6. The peptide of claim 5 comprising the peptide of formula I Ac-Lys-Arg-Tyr-Asp-Arg-Glu-Phe-Leu-Leu-Ala-Phe-Gln-Phe-Nle-R11 (SEQ ID NO: 6), wherein R11 is a cell penetrating peptide (CPP) of about 5 to about 20 amino acids.

7. The peptide of claim 6, wherein R11 is Val-Tyr-Asp-Leu-Gly-Leu-Arg-Arg-Leu-Arg-Gln-Arg-Arg-Arg-Leu-Arg-Arg (SEQ ID NO: 5).

8. The peptide of claim of claim 5, wherein the peptide consists of SEQ ID NO: 7.

9. The cell-penetrating peptide of claim 4, wherein the peptide comprises SEQ ID NOS: 9-11 and 27-44 and wherein further the amino acid sequence motif is Tyr-Trp-Leu-Leu-Ala-Leu-Phe-Val-Tyr (SEQ ID NO: 2).

10. The peptide of claim 9 comprising an amino acid sequence of Ac-Met-Ala-R1-Leu-R2-Tyr-Trp-Leu-Leu-Ala-Leu-Phe-Val-Tyr-Met-Trp-Thr-Asp-Leu-R3-Leu-R4-Lys- Lys-Arg-Pro-Lys-Pro-NH2 (SEQ ID NO. 8), wherein R1 is Lys or Asn, R2 is Lys or Ala, R3 is Leu or Arg and R4 is Phe or t-ButAla.

11. The peptide of claim 10, wherein the peptide is selected from the group consisting of SEQ ID NOs 9, 10 or 11.

12. The peptide of claim 10, wherein the peptide is SEQ ID NO. 9.

13. The peptide of claim 10, wherein the peptide is SEQ ID NO. 10.

14. The peptide of claim 10, wherein the peptide is SEQ ID NO. 11.

* * * * *

SEQUENCE LISTING

```
<160> NUMBER OF SEQ ID NOS: 91

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (6)..(7)
<223> OTHER INFORMATION: Leu or Nle
<220> FEATURE:
<221> NAME/KEY: MOD_RES
<222> LOCATION: (8)..(8)
<223> OTHER INFORMATION: Any amino acid

<400> SEQUENCE: 1

Tyr Xaa Xaa Xaa Xaa Leu Leu Xaa Phe
1               5

<210> SEQ ID NO 2
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Tyr Trp Leu Leu Ala Leu Phe Val Tyr
1               5

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Lys, Gln, Arg or Ala
<220> FEATURE:
<221> NAME/KEY: MOD_RES
<222> LOCATION: (4)..(4)
<223> OTHER INFORMATION: Asp, Asn or Ala
<220> FEATURE:
<221> NAME/KEY: MOD_RES
<222> LOCATION: (6)..(6)
<223> OTHER INFORMATION: Glu, Lys, Cys, Ala, Gln or Phe
<220> FEATURE:
<221> NAME/KEY: MOD_RES
<222> LOCATION: (10)..(10)
<223> OTHER INFORMATION: Asp, Cys, Ala or Aib
<220> FEATURE:
<221> NAME/KEY: MOD_RES
<222> LOCATION: (14)..(14)
<223> OTHER INFORMATION: Met, Ala, (D)Met or Nle
<220> FEATURE:
<221> NAME/KEY: MOD_RES
<222> LOCATION: (15)..(15)
<223> OTHER INFORMATION: Pro, (D)Pro, Ala or not present
<220> FEATURE:
<221> NAME/KEY: MOD_RES
<222> LOCATION: (16)..(16)
<223> OTHER INFORMATION: Ala, (D)Ala or not present
<220> FEATURE:
<221> NAME/KEY: MOD_RES
<222> LOCATION: (17)..(36)
<223> OTHER INFORMATION: Any amino acid and this region may encompass 5
      to 20 residues
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 3

Lys Xaa Tyr Xaa Arg Xaa Phe Leu Leu Xaa Phe Gln Phe Xaa Xaa Ala
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa
        35

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Met, Ala, (D)Met or Nle
<220> FEATURE:
<221> NAME/KEY: MOD_RES
<222> LOCATION: (4)..(4)
<223> OTHER INFORMATION: Pro, (D)Pro, Ala or not present
<220> FEATURE:
<221> NAME/KEY: MOD_RES
<222> LOCATION: (5)..(5)
<223> OTHER INFORMATION: Ala, (D)Ala or not present
<220> FEATURE:
<221> NAME/KEY: MOD_RES
<222> LOCATION: (6)..(25)
<223> OTHER INFORMATION: Any amino acid and this region may encompass 5
      to 20 residues

<400> SEQUENCE: 4

Gln Phe Xaa Xaa Ala Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Tyr Asp Leu Gly Leu Arg Arg Leu Arg Gln Arg Arg Leu Arg
1               5                   10                  15

Arg

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Nle
<220> FEATURE:
<221> NAME/KEY: MOD_RES
<222> LOCATION: (15)..(34)
<223> OTHER INFORMATION: Any amino acid and this region may encompass 5
      to 20 residues

<400> SEQUENCE: 6

Lys Arg Tyr Asp Arg Glu Phe Leu Leu Ala Phe Gln Phe Leu Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 7
<211> LENGTH: 31
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 7

Lys Arg Tyr Asp Arg Glu Phe Leu Leu Ala Phe Gln Phe Leu Val Tyr
1               5                   10                  15

Asp Leu Gly Leu Arg Arg Leu Arg Gln Arg Arg Leu Arg Arg
            20                  25                  30

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Lys or Asn
<220> FEATURE:
<221> NAME/KEY: MOD_RES
<222> LOCATION: (5)..(5)
<223> OTHER INFORMATION: Lys or Ala
<220> FEATURE:
<221> NAME/KEY: MOD_RES
<222> LOCATION: (20)..(20)
<223> OTHER INFORMATION: Leu or Arg
<220> FEATURE:
<221> NAME/KEY: MOD_RES
<222> LOCATION: (22)..(22)
<223> OTHER INFORMATION: Phe or tButAla
<220> FEATURE:
<223> OTHER INFORMATION: C-term NH2

<400> SEQUENCE: 8

Met Ala Xaa Leu Xaa Tyr Trp Leu Leu Ala Leu Phe Val Tyr Met Trp
1               5                   10                  15

Thr Asp Leu Xaa Leu Xaa Lys Lys Arg Pro Lys Pro
            20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 9

Met Ala Lys Leu Lys Tyr Trp Leu Leu Ala Leu Phe Val Tyr Met Trp
1               5                   10                  15

Thr Asp Leu Leu Leu Phe Lys Lys Arg Pro Lys Pro
            20                  25
```

```
<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 10

Met Ala Asn Leu Ala Tyr Trp Leu Leu Ala Leu Phe Val Tyr Met Trp
1               5                   10                  15

Thr Asp Leu Arg Leu Phe Lys Lys Arg Pro Lys Pro
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (22)..(22)
<223> OTHER INFORMATION: tBuAla
<220> FEATURE:
<223> OTHER INFORMATION: C-term NH2

<400> SEQUENCE: 11

Met Ala Asn Leu Ala Tyr Trp Leu Leu Ala Leu Phe Val Tyr Met Trp
1               5                   10                  15

Thr Asp Leu Arg Leu Ala Lys Lys Arg Pro Lys Pro
            20                  25

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 12

Met Val Lys Tyr Lys Ile Gly Ser Leu Leu Leu Phe Leu Phe Val Ala
1               5                   10                  15

Met Trp Ser Asp Val Gly Leu Cys Lys Lys Arg Pro Lys Pro
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2
```

```
<400> SEQUENCE: 13

Met Val Lys Ser Lys Tyr Gly Ser Trp Ile Leu Leu Leu Phe Val Ala
1               5                   10                  15

Met Trp Ser Asp Val Gly Leu Cys Lys Lys Arg Pro Lys Pro
                20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 14

Met Tyr Lys Ser Lys Ile Leu Leu Trp Phe Leu Val Leu Phe Val Ala
1               5                   10                  15

Met Trp Ser Asp Val Gly Leu Cys Lys Lys Arg Pro Lys Pro
                20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 15

Met Val Lys Ser Lys Ile Tyr Ser Trp Ile Leu Leu Leu Phe Phe Ala
1               5                   10                  15

Met Trp Ser Asp Val Gly Leu Cys Lys Lys Arg Pro Lys Pro
                20                  25                  30

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 16

Met Ala Asn Leu Gly Tyr Trp Leu Leu Ala Leu Phe Val Tyr Met Trp
1               5                   10                  15

Thr Asp Leu Leu Leu Phe Lys Lys Arg Pro Lys Pro
                20                  25

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: N-term Ac
<220> FEATURE:
<223> OTHER INFORMATION: C-term NH2

<400> SEQUENCE: 17

Met Val Lys Tyr Lys Ile Ala Ser Leu Leu Leu Phe Leu Phe Val Ala
1               5                   10                  15

Met Trp Ser Asp Val Ala Leu Ala Lys Lys Arg Pro Lys Pro
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 18

Met Val Lys Tyr Lys Ile Ala Ser Leu Leu Leu Phe Leu Phe Val Ala
1               5                   10                  15

Met Trp Ser Asp Val Lys Leu Lys Lys Lys Arg Pro Lys Pro
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 19

Met Tyr Lys Ser Lys Ile Leu Leu Trp Phe Leu Val Leu Phe Val Ala
1               5                   10                  15

Met Trp Ser Asp Val Ala Leu Ala Lys Lys Arg Pro Lys Pro
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 20

Met Val Lys Ser Lys Ile Tyr Ser Trp Ile Leu Leu Leu Phe Phe Ala
1               5                   10                  15

Met Trp Ser Asp Val Ala Leu Ala Lys Lys Arg Pro Lys Pro
            20                  25                  30
```

-continued

```
<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 21

Met Val Lys Ser Lys Ile Tyr Ser Trp Ile Leu Leu Phe Phe Ala
1               5                   10                  15

Met Trp Ser Asp Val Lys Leu Lys Lys Arg Pro Lys Pro
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 22

Lys Arg Tyr Asp Arg Glu Phe Leu Leu Ala Phe Gln Phe Leu Arg Arg
1               5                   10                  15

Leu Arg Gln Arg Arg Arg Leu Arg Arg Glu Arg Val Arg Ala
            20                  25                  30

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 23

Lys Arg Tyr Asp Arg Glu Phe Leu Leu Ala Phe Gln Phe Leu Val Tyr
1               5                   10                  15

Asp Leu Gly Leu Arg Arg Leu Arg Gln Arg Arg Arg Leu Arg Arg Glu
            20                  25                  30

Arg Val Arg Ala
        35

<210> SEQ ID NO 24
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (38)..(38)
<223> OTHER INFORMATION: Nle
<220> FEATURE:
<223> OTHER INFORMATION: C-term NH2

<400> SEQUENCE: 24

Ala Arg Val Tyr Asp Leu Gly Leu Arg Leu Arg Gln Arg Arg
1               5                   10                  15

Leu Arg Arg Glu Arg Val Arg Ala Lys Arg Tyr Asp Arg Glu Phe Leu
            20                  25                  30

Leu Ala Phe Gln Phe Leu
        35

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 25

Gly Ala Ala Glu Ala Ala Ala Tyr Val Tyr Asp Leu Leu Leu Arg Phe
1               5                   10                  15

Leu Arg Gln Arg Arg Arg Leu Arg Arg Glu Arg Val Arg Ala
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<223> OTHER INFORMATION: C-term NH2

<400> SEQUENCE: 26

Gly Ala Ala Glu Ala Ala Ala Arg Val Tyr Asp Leu Gly Leu Arg Arg
1               5                   10                  15

Leu Arg Gln Arg Arg Tyr Leu Arg Arg Glu Leu Leu Arg Phe
            20                  25                  30

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2
```

<400> SEQUENCE: 27

Met Ala Ala Leu Ala Tyr Trp Leu Leu Ala Leu Phe Val Tyr Met Trp
1               5                   10                  15

Thr Asp Leu Leu Leu Phe Lys Lys Arg Pro Lys Pro
            20                  25

<210> SEQ ID NO 28
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (20)..(20)
<223> OTHER INFORMATION: Nle
<220> FEATURE:
<223> OTHER INFORMATION: C-term NH2

<400> SEQUENCE: 28

Met Ala Ala Leu Ala Tyr Trp Leu Leu Ala Leu Phe Val Tyr Met Trp
1               5                   10                  15

Thr Asp Leu Leu Leu Phe Lys Lys Arg Pro Lys Pro
            20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (20)..(20)
<223> OTHER INFORMATION: Nle
<220> FEATURE:
<223> OTHER INFORMATION: C-term NH2

<400> SEQUENCE: 29

Met Ala Lys Leu Lys Tyr Trp Leu Leu Ala Leu Phe Val Tyr Met Trp
1               5                   10                  15

Thr Asp Leu Leu Leu Phe Lys Lys Arg Pro Lys Pro
            20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (22)..(22)
<223> OTHER INFORMATION: tBuAla
<220> FEATURE:
<223> OTHER INFORMATION: C-term NH2

```
<400> SEQUENCE: 30

Met Ala Lys Leu Lys Tyr Trp Leu Leu Ala Leu Phe Val Tyr Met Trp
1               5                   10                  15

Thr Asp Leu Leu Leu Ala Lys Lys Arg Pro Lys Pro
            20                  25

<210> SEQ ID NO 31
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 31

Leu Ala Tyr Trp Leu Leu Ala Leu Phe Val Tyr Met Trp Thr Asp Leu
1               5                   10                  15

Arg Leu Phe Lys Lys Arg Pro Lys Pro
            20                  25

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (19)..(19)
<223> OTHER INFORMATION: tBuAla
<220> FEATURE:
<223> OTHER INFORMATION: C-term NH2

<400> SEQUENCE: 32

Leu Ala Tyr Trp Leu Leu Ala Leu Phe Val Tyr Met Trp Thr Asp Leu
1               5                   10                  15

Arg Leu Ala Lys Lys Arg Pro Lys Pro
            20                  25

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 33

Leu Ala Tyr Trp Leu Leu Ala Leu Phe Val Tyr Met Trp Thr Asp Leu
1               5                   10                  15

Arg Leu Ala Lys Lys Arg Pro Lys Pro
            20                  25
```

<210> SEQ ID NO 34
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 34

Ala Asn Leu Ala Tyr Trp Leu Leu Ala Leu Phe Val Tyr Met Trp Thr
1               5                   10                  15

Asp Leu Arg Leu Phe Lys Lys Arg Pro Lys Pro
            20                  25

<210> SEQ ID NO 35
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 35

Asn Leu Ala Tyr Trp Leu Leu Ala Leu Phe Val Tyr Met Trp Thr Asp
1               5                   10                  15

Leu Arg Leu Phe Lys Lys Arg Pro Lys Pro
            20                  25

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 36

Ala Tyr Trp Leu Leu Ala Leu Phe Val Tyr Met Trp Thr Asp Leu Arg
1               5                   10                  15

Leu Phe Lys Lys Arg Pro Lys Pro
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

```
<400> SEQUENCE: 37

Tyr Trp Leu Leu Ala Leu Phe Val Tyr Met Trp Thr Asp Leu Arg Leu
1               5                   10                  15

Phe Lys Lys Arg Pro Lys Pro
            20

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 38

Met Ala Asn Leu Ala Tyr Trp Leu Leu Ala Leu Phe Val Tyr Leu Trp
1               5                   10                  15

Thr Asp Leu Arg Leu Phe Lys Lys Arg Pro Lys Pro
            20                  25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (15)..(15)
<223> OTHER INFORMATION: Nle
<220> FEATURE:
<223> OTHER INFORMATION: C-term NH2

<400> SEQUENCE: 39

Met Ala Asn Leu Ala Tyr Trp Leu Leu Ala Leu Phe Val Tyr Leu Trp
1               5                   10                  15

Thr Asp Leu Arg Leu Phe Lys Lys Arg Pro Lys Pro
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 40

Met Ala Asn Leu Ala Tyr Trp Leu Leu Ala Leu Phe Val Tyr Lys Trp
1               5                   10                  15

Thr Asp Leu Arg Leu Phe Lys Lys Arg Pro Lys Pro
            20                  25
```

```
<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 41

Met Ala Asn Leu Ala Tyr Trp Leu Leu Ala Leu Phe Val Tyr Arg Trp
1               5                   10                  15

Thr Asp Leu Arg Leu Phe Lys Lys Arg Pro Lys Pro
            20                  25

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 42

Met Ala Asn Leu Ala Tyr Trp Leu Leu Ala Leu Phe Val Tyr Met Phe
1               5                   10                  15

Thr Asp Leu Arg Leu Phe Lys Lys Arg Pro Lys Pro
            20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (16)..(16)
<223> OTHER INFORMATION: 1Nal
<220> FEATURE:
<223> OTHER INFORMATION: C-term NH2

<400> SEQUENCE: 43

Met Ala Asn Leu Ala Tyr Trp Leu Leu Ala Leu Phe Val Tyr Met Ala
1               5                   10                  15

Thr Asp Leu Arg Leu Phe Lys Lys Arg Pro Lys Pro
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (16)..(16)
<223> OTHER INFORMATION: 2Nal
<220> FEATURE:
<223> OTHER INFORMATION: C-term NH2

<400> SEQUENCE: 44

Met Ala Asn Leu Ala Tyr Trp Leu Leu Ala Leu Phe Val Tyr Met Ala
1               5                   10                  15

Thr Asp Leu Arg Leu Phe Lys Lys Arg Pro Lys Pro
            20                  25

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term NH2

<400> SEQUENCE: 45

Met Val Lys Tyr Lys Ile Ala Ser Leu Leu Leu Phe Leu Phe Val Ala
1               5                   10                  15

Met Trp Ser Asp Val Ala Leu Ala Lys Lys Arg Pro Lys Pro
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: Nle
<220> FEATURE:
<223> OTHER INFORMATION: C-term NH2

<400> SEQUENCE: 46

Met Tyr Lys Ser Lys Ile Leu Leu Trp Phe Leu Val Leu Phe Val Ala
1               5                   10                  15

Met Trp Ser Asp Val Lys Leu Lys Lys Arg Pro Lys Pro
            20                  25                  30

<210> SEQ ID NO 47
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Thr-Obzl
```

```
<220> FEATURE:
<221> NAME/KEY: MOD_RES
<222> LOCATION: (22)..(22)
<223> OTHER INFORMATION: tBuAla
<220> FEATURE:
<223> OTHER INFORMATION: C-term NH2

<400> SEQUENCE: 47

Met Ala Lys Leu Lys Tyr Trp Leu Leu Ala Leu Phe Val Thr Met Trp
1               5                   10                  15

Thr Asp Leu Leu Leu Ala Lys Lys Arg Pro
            20                  25

<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Thr-Obzl
<220> FEATURE:
<221> NAME/KEY: MOD_RES
<222> LOCATION: (23)..(23)
<223> OTHER INFORMATION: tBuAla
<220> FEATURE:
<223> OTHER INFORMATION: C-term NH2

<400> SEQUENCE: 48

Met Ala Asn Leu Ala Tyr Trp Leu Leu Ala Leu Phe Val Thr Tyr Met
1               5                   10                  15

Trp Thr Asp Leu Arg Leu Ala Lys Lys Arg Pro Lys Pro
            20                  25

<210> SEQ ID NO 49
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 49

Leu Ala Tyr Trp Leu Leu Ala Leu Phe Val Ala Met Trp Thr Asp Leu
1               5                   10                  15

Arg Leu Phe Lys Lys Arg Pro Lys Pro
            20                  25

<210> SEQ ID NO 50
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2
```

```
<400> SEQUENCE: 50

Trp Leu Leu Ala Leu Phe Val Tyr Met Trp Thr Asp Leu Arg Leu Phe
1               5                   10                  15

Lys Lys Arg Pro Lys Pro
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 51

Leu Leu Ala Leu Phe Val Tyr Met Trp Thr Asp Leu Arg Leu Phe Lys
1               5                   10                  15

Lys Arg Pro Lys Pro
            20

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 52

Lys Gln Tyr Asp Arg Glu Phe Leu Leu Asp Phe Gln Phe Met Pro Ala
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 53

Lys Gln Tyr Asp Arg Glu Phe Leu Leu Asp Phe Gln Phe Met Pro
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2
```

```
<400> SEQUENCE: 54

Lys Gln Tyr Asp Arg Glu Phe Leu Leu Asp Phe Gln Phe Met
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 55

Lys Gln Tyr Asp Arg Glu Phe Leu Leu Asp Phe Gln Phe
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 56

Lys Gln Tyr Asp Arg Glu Phe Leu Leu Asp Phe
1               5                   10

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 57

Lys Gln Tyr Asp Arg Glu Phe Leu Leu Asp Phe Gln Phe Met Ala Ala
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 58

Lys Gln Tyr Asp Arg Glu Phe Leu Leu Asp Phe Gln Phe Ala Pro Ala
1               5                   10                  15
```

```
<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 59

Lys Gln Tyr Asp Arg Glu Phe Leu Leu Ala Phe Gln Phe Met Pro Ala
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 60

Lys Gln Tyr Asp Arg Ala Phe Leu Leu Asp Phe Gln Phe Met Pro Ala
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 61

Lys Gln Tyr Ala Arg Glu Phe Leu Leu Asp Phe Gln Phe Met Pro Ala
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 62

Lys Ala Tyr Asp Arg Glu Phe Leu Leu Asp Phe Gln Phe Met Pro Ala
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<223> OTHER INFORMATION: C-term NH2

<400> SEQUENCE: 63

Ala Gln Tyr Asp Arg Glu Phe Leu Leu Asp Phe Gln Phe Met Pro Ala
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (16)..(16)
<223> OTHER INFORMATION: (D)Ala
<220> FEATURE:
<223> OTHER INFORMATION: C-term NH2

<400> SEQUENCE: 64

Lys Gln Tyr Asp Arg Glu Phe Leu Leu Asp Phe Gln Phe Met Pro Ala
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (15)..(15)
<223> OTHER INFORMATION: (D)Pro
<220> FEATURE:
<223> OTHER INFORMATION: C-term NH2

<400> SEQUENCE: 65

Lys Gln Tyr Asp Arg Glu Phe Leu Leu Asp Phe Gln Phe Met Pro Ala
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: (D)Met
<220> FEATURE:
<223> OTHER INFORMATION: C-term NH2

<400> SEQUENCE: 66

Lys Gln Tyr Asp Arg Glu Phe Leu Leu Asp Phe Gln Phe Met Pro Ala
1               5                   10                  15
```

```
<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (13)..(13)
<223> OTHER INFORMATION: (D)Phe
<220> FEATURE:
<223> OTHER INFORMATION: C-term NH2

<400> SEQUENCE: 67

Lys Gln Tyr Asp Arg Glu Phe Leu Leu Asp Phe Gln Phe Met Pro Ala
1               5                   10                  15

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 68

Tyr Asp Arg Glu Phe Leu Leu Asp Phe Gln Phe Met
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 69

Tyr Asp Arg Glu Phe Leu Leu Asp Phe Gln Phe
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (12)..(12)
<223> OTHER INFORMATION: Nle
<220> FEATURE:
<223> OTHER INFORMATION: C-term NH2

<400> SEQUENCE: 70

Tyr Asp Arg Glu Phe Leu Leu Asp Phe Gln Phe Leu
1               5                   10
```

```
<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (12)..(12)
<223> OTHER INFORMATION: Nle
<220> FEATURE:
<223> OTHER INFORMATION: C-term NH2

<400> SEQUENCE: 71

Tyr Asp Arg Gln Phe Leu Leu Asp Phe Gln Phe Leu
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (12)..(12)
<223> OTHER INFORMATION: Nle
<220> FEATURE:
<223> OTHER INFORMATION: C-term NH2

<400> SEQUENCE: 72

Tyr Asp Arg Glu Phe Leu Leu Ala Phe Gln Phe Leu
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (12)..(12)
<223> OTHER INFORMATION: Nle
<220> FEATURE:
<223> OTHER INFORMATION: C-term NH2

<400> SEQUENCE: 73

Tyr Asp Arg Glu Phe Leu Leu Xaa Phe Gln Phe Leu
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (12)..(12)
<223> OTHER INFORMATION: Nle
<220> FEATURE:
<223> OTHER INFORMATION: C-term NH2

<400> SEQUENCE: 74

Tyr Asn Arg Glu Phe Leu Leu Asp Phe Gln Phe Leu
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (12)..(12)
<223> OTHER INFORMATION: Nle
<220> FEATURE:
<223> OTHER INFORMATION: C-term NH2

<400> SEQUENCE: 75

Tyr Asn Arg Gln Phe Leu Leu Asp Phe Gln Phe Leu
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Mamb
<220> FEATURE:
<221> NAME/KEY: MOD_RES
<222> LOCATION: (9)..(9)
<223> OTHER INFORMATION: Nle
<220> FEATURE:
<223> OTHER INFORMATION: C-term NH2

<400> SEQUENCE: 76

Tyr Xaa Leu Leu Ala Phe Gln Phe Leu
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Mamp
```

```
<220> FEATURE:
<221> NAME/KEY: MOD_RES
<222> LOCATION: (9)..(9)
<223> OTHER INFORMATION: Nle
<220> FEATURE:
<223> OTHER INFORMATION: C-term NH2

<400> SEQUENCE: 77

Tyr Xaa Leu Leu Ala Phe Gln Phe Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: NVa
<220> FEATURE:
<221> NAME/KEY: MOD_RES
<222> LOCATION: (9)..(9)
<223> OTHER INFORMATION: Nle
<220> FEATURE:
<223> OTHER INFORMATION: C-term NH2

<400> SEQUENCE: 78

Tyr Val Leu Leu Ala Phe Gln Phe Leu
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: 5Ava
<220> FEATURE:
<221> NAME/KEY: MOD_RES
<222> LOCATION: (9)..(9)
<223> OTHER INFORMATION: Nle
<220> FEATURE:
<223> OTHER INFORMATION: C-term NH2

<400> SEQUENCE: 79

Phe Xaa Leu Leu Ala Phe Gln Phe Leu
1               5

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Nle
```

```
<220> FEATURE:
<223> OTHER INFORMATION: C-term NH2

<400> SEQUENCE: 80

Lys Arg Tyr Asp Arg Glu Phe Leu Leu Ala Phe Gln Phe Leu
1               5                   10

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 81

Gln Tyr Asp Arg Glu Phe Leu Leu Asp Phe Gln Phe Met Pro Ala
1               5                   10                  15

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 82

Tyr Asp Arg Glu Phe Leu Leu Asp Phe Gln Phe Met Pro Ala
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (D)Lys
<220> FEATURE:
<223> OTHER INFORMATION: C-term NH2

<400> SEQUENCE: 83

Lys Gln Tyr Asp Arg Glu Phe Leu Leu Asp Phe Gln Phe Met Pro Ala
1               5                   10                  15

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
```

```
<220> FEATURE:
<221> NAME/KEY: MOD_RES
<222> LOCATION: (14)..(14)
<223> OTHER INFORMATION: Nle
<220> FEATURE:
<223> OTHER INFORMATION: C-term NH2

<400> SEQUENCE: 84

Lys Arg Phe Asp Arg Glu Phe Leu Leu Ala Phe Gln Phe Leu
1               5                   10

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (16)..(16)
<223> OTHER INFORMATION: Nle
<220> FEATURE:
<223> OTHER INFORMATION: C-term NH2

<400> SEQUENCE: 85

Lys Arg Lys Arg Phe Asp Arg Glu Phe Leu Leu Ala Phe Gln Phe Leu
1               5                   10                  15

<210> SEQ ID NO 86
<211> LENGTH: 217
<212> TYPE: PRT
<213> ORGANISM: Homo sapiens

<400> SEQUENCE: 86

Met Ala Thr Val Glu Pro Glu Thr Thr Pro Thr Pro Asn Pro Pro Thr
1               5                   10                  15

Thr Glu Glu Glu Lys Thr Glu Ser Asn Gln Glu Val Ala Asn Pro Glu
                20                  25                  30

His Tyr Ile Lys His Pro Leu Gln Asn Arg Trp Ala Leu Trp Phe Phe
            35                  40                  45

Lys Asn Asp Lys Ser Lys Thr Trp Gln Ala Asn Leu Arg Leu Ile Ser
        50                  55                  60

Lys Phe Asp Thr Val Glu Asp Phe Trp Ala Leu Tyr Asn His Ile Gln
65                  70                  75                  80

Leu Ser Ser Asn Leu Met Pro Gly Cys Asp Tyr Ser Leu Phe Lys Asp
                85                  90                  95

Gly Ile Glu Pro Met Trp Glu Asp Glu Lys Asn Lys Arg Gly Gly Arg
            100                 105                 110

Trp Leu Ile Thr Leu Asn Lys Gln Gln Arg Arg Ser Asp Leu Asp Arg
        115                 120                 125

Phe Trp Leu Glu Thr Leu Leu Cys Leu Ile Gly Glu Ser Phe Asp Asp
130                 135                 140

Tyr Ser Asp Asp Val Cys Gly Ala Val Val Asn Val Arg Ala Lys Gly
145                 150                 155                 160

Asp Lys Ile Ala Ile Trp Thr Thr Glu Cys Glu Asn Arg Glu Ala Val
                165                 170                 175

Thr His Ile Gly Arg Val Tyr Lys Glu Arg Leu Gly Leu Pro Pro Lys
            180                 185                 190
```

```
Ile Val Ile Gly Tyr Gln Ser His Ala Asp Thr Ala Thr Lys Ser Gly
            195                 200                 205

Ser Thr Thr Lys Asn Arg Phe Val Val
        210                 215

<210> SEQ ID NO 87
<211> LENGTH: 190
<212> TYPE: PRT
<213> ORGANISM: Homo sapiens

<400> SEQUENCE: 87

Val Ala Asn Pro Glu His Tyr Ile Lys His Pro Leu Gln Asn Arg Trp
1               5                   10                  15

Ala Leu Trp Phe Phe Lys Asn Asp Lys Ser Lys Thr Trp Gln Ala Asn
            20                  25                  30

Leu Arg Leu Ile Ser Lys Phe Asp Thr Val Glu Asp Phe Trp Ala Leu
        35                  40                  45

Tyr Asn His Ile Gln Leu Ser Ser Asn Leu Met Pro Gly Cys Asp Tyr
    50                  55                  60

Ser Leu Phe Lys Asp Gly Ile Glu Pro Met Trp Glu Asp Glu Lys Asn
65                  70                  75                  80

Lys Arg Gly Gly Arg Trp Leu Ile Thr Leu Asn Lys Gln Gln Arg Arg
                85                  90                  95

Ser Asp Leu Asp Arg Phe Trp Leu Glu Thr Leu Leu Cys Leu Ile Gly
            100                 105                 110

Glu Ser Phe Asp Asp Tyr Ser Asp Asp Val Cys Gly Ala Val Val Asn
        115                 120                 125

Val Arg Ala Lys Gly Asp Lys Ile Ala Ile Trp Thr Thr Glu Cys Glu
    130                 135                 140

Asn Arg Glu Ala Val Thr His Ile Gly Arg Val Tyr Lys Glu Arg Leu
145                 150                 155                 160

Gly Leu Pro Pro Lys Ile Val Ile Gly Tyr Gln Ser His Ala Asp Thr
                165                 170                 175

Ala Thr Lys Ser Gly Ser Thr Thr Lys Asn Arg Phe Val Val
            180                 185                 190

<210> SEQ ID NO 88
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Val Ala Asn Pro Glu His Tyr Ile Lys His Pro Leu Gln Asn Arg Trp
1               5                   10                  15

Ala Leu Trp Phe Phe Lys Asn Asp Lys Ser Lys Thr Trp Gln Ala Asn
            20                  25                  30

Leu Arg Leu Ile Ser Lys Phe Asp Thr Val Glu Asp Phe Trp Ala Leu
        35                  40                  45

Tyr Asn His Ile Gln Leu Ser Ser Asn Leu Met Pro Gly Cys Asp Tyr
    50                  55                  60

Ser Leu Phe Lys Asp Gly Ile Glu Pro Met Trp Glu Asp Glu Lys Asn
65                  70                  75                  80

Lys Arg Gly Gly Arg Trp Leu Ile Thr Leu Asn Lys Gln Gln Arg Arg
                85                  90                  95
```

```
Ser Asp Leu Asp Arg Phe Trp Leu Glu Thr Leu Leu Cys Leu Ile Gly
            100                 105                 110

Glu Ser Phe Asp Asp Tyr Ser Asp Asp Val Cys Gly Ala Val Val Asn
        115                 120                 125

Val Arg Ala Lys Gly Asp Lys Ile Ala Ile Trp Thr Thr Glu Cys Glu
    130                 135                 140

Asn Arg Glu Ala Val Thr His Ile Gly Arg Val Tyr Lys Glu Arg Leu
145                 150                 155                 160

Gly Leu Pro Pro Lys Ile Val Ile Gly Tyr Gln Ser His Ala Asp Thr
                165                 170                 175

Ala Thr Lys Ser Gly Ser Thr Thr Lys Asn Arg Phe Val His His
            180                 185                 190

His His His His
        195

<210> SEQ ID NO 89
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (1)..(25)
<223> OTHER INFORMATION: Any amino acid and this region may encompass 8
      to 25 residues
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (35)..(59)
<223> OTHER INFORMATION: Any amino acid and this region may encompass 8
      to 25 residues
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 89

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Tyr Xaa Xaa Xaa Xaa Leu Leu
            20                  25                  30
```

```
Xaa Phe Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
        50                  55

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 90

Tyr Xaa Xaa Xaa Xaa Leu Leu Xaa Phe
1               5

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (16)..(16)
<223> OTHER INFORMATION: Lys(Aha-Bio)
<220> FEATURE:
<223> OTHER INFORMATION: C-term NH2

<400> SEQUENCE: 91

Lys Gln Tyr Asp Arg Glu Phe Leu Leu Asp Phe Gln Phe Met Pro Lys
1               5                   10                  15
```